US006103243A

United States Patent [19]
Russell-Jones et al.

[11] Patent Number: 6,103,243
[45] Date of Patent: Aug. 15, 2000

[54] ORAL VACCINES

[75] Inventors: Gregory John Russell-Jones, Willoughby; Peter Howe, West Pennant Hills; Henry James de Aizpurua, Bexley; Keith Norman Rand, Chatswood, all of United Kingdom

[73] Assignee: Biotechnology Australia PTY, LTD, New South Wales, Australia

[21] Appl. No.: 08/458,814

[22] Filed: Jun. 2, 1995

Related U.S. Application Data

[62] Division of application No. 08/327,822, Oct. 18, 1994, which is a continuation of application No. 08/158,478, Nov. 29, 1993, which is a continuation of application No. 07/015,810, filed as application No. PCT/AU86/00135, May 14, 1986.

[30] Foreign Application Priority Data

May 15, 1985 [AU] Australia .............................. PH 0566
Oct. 25, 1985 [AU] Australia .............................. PH 3104

[51] Int. Cl.$^7$ .................................................. A61K 39/385
[52] U.S. Cl. .................................. 424/195.11; 424/184.1; 424/193.1
[58] Field of Search ............................. 424/184.1, 252.1, 424/195.11

[56] References Cited

U.S. PATENT DOCUMENTS

| | | |
|---|---|---|
| 4,268,435 | 5/1981 | Bahl . |
| 4,302,386 | 11/1981 | Stevens . |
| 4,310,455 | 1/1982 | Bahl . |
| 4,313,871 | 2/1982 | Bahl . |
| 4,411,888 | 10/1983 | Klipstein et al. . |
| 4,470,967 | 9/1984 | Gouch et al. . |
| 4,526,716 | 7/1985 | Stevens . |
| 4,608,251 | 8/1986 | Mia . |
| 4,644,059 | 2/1987 | Gordon . |
| 4,650,673 | 3/1987 | Johnston . |
| 4,664,911 | 5/1987 | Uhr et al. . |
| 4,727,136 | 2/1988 | Jennings et al. . |
| 4,751,064 | 6/1988 | Sela et al. . |
| 4,761,283 | 8/1988 | Anderson . |
| 4,780,312 | 10/1988 | Talwar . |
| 4,830,852 | 5/1989 | Marburg et al. . |
| 4,859,765 | 8/1989 | Nestor, Jr. et al. . |

FOREIGN PATENT DOCUMENTS

| | | |
|---|---|---|
| 0-060129 | 9/1982 | European Pat. Off. . |
| 0-177343 | 4/1986 | European Pat. Off. . |
| 0-178867 | 4/1986 | European Pat. Off. . |
| 2-306684 | 11/1976 | France . |
| 8-303971 | 11/1983 | WIPO . |
| 3-01007 | 2/1984 | WIPO . |

OTHER PUBLICATIONS

Szoka, P. et al., A General Method for Retrieving the components of a Genetically Engineered Fusion Protein, DNA 5, 11–20 (1986). see entire article.
Shaha et al., (1986), "Immunol. Approaches contracept Prouet Fertil.", 1985 (1986)143–50.
Ed Talwar, GP Plenum. NY, NY as Chem Abstract 106:207 854 on p. 80, 1987.
Gupta et al. AJRIM 7(3): 104–108 (1985) abstract 13 Biol Abstract 80(11):98754 (ref No.).
Govery et al, AJRIM 8(2) 43–47A Biol Abstract 80(11) ref No. 98575 (1985).
Lycke et al., (1986), Immunology 59: 301–308.
Liang et al. (1988), J. Immunol 141: 1495–1501.
Alan et al., (1989) Vaccine 7: 129–131.
Dallas et al., (1979) J. Bacteriof. 139: 850–858.
McKenzie et al., (1984), J. Immunol. 133(4):1818–1824.
"Induction of Tolerance to a Soluble Protein Antigen by Oral Administration", Immunology 27:631–639, (1974).
Tomasi, T.B., "Oral Tolerance", Transplantation, 29, 353, 1980.
Mowat, A., McL., "The role of antigen recognition & supressor cells in mice with oral tolerance to ovalbumin", Immun.; 56, 253–260, 1985.
Mowat, A., McL. et al., "Immunological response to fed protein antigens in mice", Immun. 50, 547–554, 1983.
Ngan, J. et al., "Suppressor T cells for IgE & IgG in peyers patches of mice tolerant by the oral administration of ovalbumin", J. Immunol. 120, 861–865, 1978.
Hanson, D.G., et al. "Inhibition of specific immune response by feeding proteins antigens", J. Immunol., 123, 2337–2443, 1979.
Richman, L.K. et al., "Antigen presentation by macrophage enriched cells from the mouse peyer's patch", Cell Immunol., 62:1100, 1981.
Rothberg, R.M. et al., "Systemic immunity after local antigenic stimulation of the lymphoid tissue of the gastro–intestinal tract", J. Immunol., 111, 1906–1913, 1973.
Bland, P.W. et al., Morphological study of antigen–sampling structures in the rat large intestine Infect. Immunol., 43, 693–699, 1984.
Gaastra, W. et al., "Host specific fimbrial adhesion of non invasive enterotoxigenic *Escherichia coli* strains", Micro Biol. Rev. 46:129 1982.
Gibbons, R. et al., "An attempt to identify the intestinal receptor for the K88 adhesion by means of a haemagglutination inhibition test using glycoproteins and fractions from sow colostrum", J. Gen. Micro Biol., 86, 228–240, 1975.
Evans, D.G. et al., "New surface associated heat–labile colonization factor antigen (CFA/11) produced by enterotoxigenic *Escherichia coli* of serogroups 06 & 08", Immunol., 21, 638–647, 1978.
Levine, M.M., et al., Haemagglutination & colonization factors in enterotoxigenic & enteropathogenic *Escherichia coli* that cause diarrhoea, J. Inf. Dis., 141, 733–737, 1980.
Morgan, R.L., et al., "Immunization of suckling pigs against enterotoxigenic *Escherichia coli*–induced diarrhoea disease by vaccinating dams with purified 987 or K99 pilli", Inf. Immun. 22, 771–777, 1978.

(List continued on next page.)

*Primary Examiner*—Paula K. Hutzell
*Assistant Examiner*—Stephen Gucker
*Attorney, Agent, or Firm*—Foley & Lardner

[57] ABSTRACT

The present invention relates to the specific stimulation of serum and secretory antibodies through mucosal presentation of antigens.

11 Claims, 1 Drawing Sheet

OTHER PUBLICATIONS de Graaf, F.K. et al., "Production purification & characterization of the fimbrial adhesion antigen F41 isolated from calf enteropathogenic *Escherichia coli* strain B41M", Infect. Immunol., 36, 751–758, 1978.

Laemmli, U.K., "Cleavage of structural proteins during the assembly of the head of bacteriophage T4" Nature (Lond), 227:680, 1970.

Salit, I.E. et al., "Intrastrain heterogeneity of *gonoccal pili* is related to capacity colony variance", J. Exp. Med. 151: 716, 1980.

Tsao, C.M. et al., "A sensitive silver strain for detecting lipopolysaccharide in polyacrylamide gels", Anal Biochem., 119, 115–119, 1982.

Isaacson, R.E et al., "*Escherichia coli* 987P Pilus, Purification & partial characterization", J. Bacterial., 146:784, 1981.

Herbert D. Phipps P.J. et al., "Carbohydrates analysis determination of total carbohydrates", Norris, J.R. et al. (ed.) Methods in Microbiology, V. 58, 1985.

Morris, J.A. et al., "Evidence for two adhesive antigens on the K99 reference strain *Escherichia coli* B41", J. Gen. Microbiol., 118:107, 1980.

Fusco, P. et al., "The purification & characterization of four types of *E. coli pili* & the specificity of *E. coli pili* for immunity colonization & adhesion", p. 60–70, 1978.

Little, J.R. et al., "Preparation of Immunogenic 2,4 dinitrophenol and 2,4,6 trintrophenyl proteins", in "Methods in Immunology and Immunochemistry", Ed. Williams, C.A. et al., p. 28.

Russel–Jones, G.J. et al., "Identification of protein antigens of group B Streptococci with special reference to the lbc antigen", J. Exp. Med., (1984) 160:476, 1984.

Avraemeus, S. et al., "Coupling of enzymes to antibodies & antigens", Scand. J. Immunol., 8, suppl. 7, 7–23, 1978.

Avrameas, S. et al., "Peroxidase labelled antibody & Fab. conjugate with enhanced intracellular penetration", Immunochem., 8, 1175–1179, 1971.

Leong et al., "Nucleotide sequence comparison between heat labile toxin B–sub–units cistrons from *Escherichia coli* of human & porcine origin", Infection & Immunity, 48, 73–77, 1985.

Schally et al., "Stimulatory & inhibitory analogues of LH–releasing hormone: Basic & clinical studies in Role of Peptides & Proteins in Control of Reproduction", McCann et al., ed. Elsevier Science Publishing Co., Inc., pp. 89–110, 1983.

Messing, J., "New M13 Vectors for cloning", Methods for Enzymology, 101, 20–78, 1983.

Befus, D. et al., (1982), "Factors involved in symbiosis and host resistance at the mucosa–parasite interface", Prog. Allergy 31;76–177.

Bienenstock, J., et al., "Mucosal Immunology", Immunology 41:249–270, (1980).

Black, M.S. et al., "Purification and partial characterization of the opacity–associated proteins of *Neisseria gonorrhea*", J. Exp. Med. 159:452–462 (1984).

Clark, S. et al., "Prevention by vaccination animal bacteria", in "Infectious diarrhoea in the young", pp. 481–487 (1985), Elsevier Science Publishers B.V. (TZIPORI, S. et al., eds.) 1985.

Cantey, J.R. et al., "Diarrhea due to *Escherichia coli* strain RDEC–1 in the rabbit. The Peyer's Patch as the initial site of attachment and colonization", J. Infectious Disease 143:440–446 1981.

Elson, C.O. et al., "Generalized systemic and mucosal immunity in mice after mucosal stimulation with cholera toxin", J. Immunology 132:2736–2740, (1984).

Fujita, K et al., "Antitoxic Immunity in Experimental Cholera. Comparison of Immunity induced perorally and parentally in mice", J. Infectious Diseases 125:647–655 (1972).

Klipstein, F.A. et al., "Protective Effect of Immunization with Heat–Labile Enterotoxin in gnotóbiotic rates monocontaminated with enterotoxigenic *Escherichia coli*", infection and Immunity 28:163–170 (1980).

Messier, B. et al., "Cell proliferation and migration as revealed by radioautography after infection of Thymidine–$H^3$ into male rates and mice", Am J. Anat. 106:247–285 (1960).

Pierce, N.F. et al., "Priming and suppression of the intentional immune response to cholera toxoid toxin by parental toxoid in rats", J. Immunology 124:306–311 (1980).

Pierce, N.F. et al., "Immunity to Experimental Cholera III. Enhanced duration of protection after sequential parenteral–oral administration of toxoid to dogs", J. Infectious Diseases 135:888–896 (1977).

Richman, L.K. et al., "Enterically induced immunological tolerance", J. Immunology 121:2429–2434 (1978).

Russel–Jones, G.J., et al., "A surface receptor specific for human IgA on groub B streptococci possessing the ibc protein antigen", J. Exp. Med. 106:1467–1475 (1984).

Svennerhold, A.M. et al., "Identification of *Escherichia coli* heat labile enterotoxin by means of ganglioside immunosorbent assy (GM1–ELISA) Procedure", Current Microbiology 1:19–23, (1978).

Toner, P.G. et al., "Intestine", pp. 55–127 in "The Digestive System: an ultra structural atlas and review", Butterworths London, (1971).

Covey, D.C. et al., "A Candidate Carrier Protein for Beta–Human Chorionic Gonadotropin: 54,000–Molecular Weight Fragment of Tetanus Toxin", Biol. Abstr. vol. 80, 98575; Am. J. Reprod. Immun. Microbiol., 1985, vol. 8, No. 2, pp. 43–47.

|  | 1 | 5 | 10 |
|---|---|---|---|
| Type 1 | Ala-Ala-Thr-Thr-Val-Asn-Gly-Gly-Thr-Val-His-Phe-Lys-Gly- | | |
| K88 | Trp-Met-Thr-Gly-Asp-Phe-Asn-Gly-Ser-Val-Asp-Ile-Gly-Gly- | | |
| K99 | Asn-Thr-Gly-The-Ile-Asn-Phe-Asn-Gly-Lys-Ile-Thr-Ser-Ala- | | |
| 987P | Ala-Pro-Val-Glu-Asn-Asn-Thr-Cys-Gln-Ala-Asn-Leu-Asp-Phe- | | |
| Neisseria | Phe-Thr-Leu-Ile-Glu-Leu-Met-Ile-Val-Ile-Ala-Ile-Val-Gly- | | |

|  | 15 | 20 | 25 |
|---|---|---|---|
| Type 1 | Glu-Val-Val-Asn-Ala-Ala- | | |
| K88 | Ser-Ile-Thr-Ala-Asp-Asp-Tyr-Arg- | | |
| K99 | Thr-Cys-Thr-Ile-Glu-Pro-Glu-Ala- | | |
| 987P | Thr-Gly-Lys-Val-Thr-Ala- x -Leu- | | |
| Neisseria | Ile-Leu-Ala-Ala-Val-Ala-Ala-Leu-Pro- | | |

FIG. 1 N-terminal amino acid sequence of the 987P pilin subunit. The N-terminal sequences of other pilin proteins are given for comparison.

ORAL VACCINES

This application is a division, of application Ser. No. 08/327,822, filed Oct. 18, 1994 which is a continuation of Ser. No. 08/158,478 filed Nov. 29, 1993 which is continuation of Ser. No. 07/015,810 filed Jan. 12, 1987 which is the national stage of International Application PCT/AU86/00135 filed May 14, 1986.

TECHNICAL FIELD

The present invention relates to the specific stimulation of serum and secretory antibodies through mucosal presentation of antigens.

BACKGROUND ART

A number of infections in mammals have sufficient deleterious effects of the mammal to warrant vaccination against the particular antigen responsible for the infection. Therefore, vaccination programmes are instituted whereby the mammal is antigenically challenged with an antigen so that an immune response is elicited to confer immunity to the mammal.

Administration of the antigen to the mammal may be through a number of routes including injection intramuscularly (i.m.), subcutaneously (s.c.), or through oral administration (per os). I.m. or s.c. injection of antigen suffers from the disadvantages that relatively specialized skills are required, it is difficult to undertake on a large scale, it is expensive, and a number of side reactions can occur to either the immunizing antigen or to the emulsifying reagent in which it is presented. Oral administration of vaccines is by contrast relatively problem free except insofar as oral feeding of a number of antigens requires relatively large quantities of antigen as the amount of material that is actually absorbed and capable of stimulating an effective immune response is usually low. Thus the amount of antigen required for oral immunization generally far exceeds that required for systemic induction of immunity. There is also one major disadvantage to the oral presentation of the large quantities of antigen required to produce an antibody response and that is that feeding of these large quantities of antigen often leads to the induction of systemic tolerance (Tomasi, 1980; Mowat, 1985; Mowat and Parrot, 1983; Ngan & Kind, 1978; Hanson et al, 1979; Richman et al. 1978; Rothberg et al., 1973).

Evidence to date suggests that in general the mechanism by which antigen is take up by the small intestine, following oral feeding, is primarily via non-specific sampling of the contents of the gut lumen by "M" cells which overlie the Peyer's Patches and other lymphoid clusters of the GALT (gut-associated-lymphoid tissue) (Bland and Britton, 1984). The subsequent sensitization of local lymphocyte populations leads to the generation of local IgA Immune responses plus the sensitization of IgG suppressor cells with concomitant suppression of serum IgG responses (Tomasi, 1980; Mowat, 1985; Mowat and Parrot, 1983; Ngan & Kind, 1978; Hanson et al, 1979; Richman et al, 1978; Rothberg et al, 1973).

It is therefore apparent that the site of antigen uptake, whether it be through the Peyer's Patches or the villous epithelium, and quite probably the amount of antigen administered, dictates the type of immune response generated by orally administered antigen. The question arises then as to whether there are any other antigens apart from cholera toxin which exhibit the ability to specifically prime the mucosal immune system upon oral challenge and/or to stimulate the humoral immune response in a dose dependant manner without inducing systemic tolerance and without the need for excessive doses of antigen.

With this view in mind we decided to investigate the possible potential of certain adhesive molecules, which have been implicated in the initial attachment of a number of intestinal pathogens, to stimulate the immune response when orally administered. These surface antigens which confer adhesive properties to a number of strains of enterotoxigenic *E. coli* (ETEC) have been identified as nonflagellar, filamentous proteinaceous appendages, or pili (Gaastra & de Graaf, 1982). Examples include the CFA I and CFA II antigens of human ETEC strains and the K88, K99, F41 and 987P pili of animal ETEC strains (Gibbons et al, 1975; Evans & Evans, 1978; Levine et al., 1980; Morgan et al., 1978; de Graaf & Roorda, 1982). In addition, we have examined the ability of a number of other proteins which have no apparent role in colonization to prime the immune system upon oral feeding. These antigens included a number of lectins a serotypic antigen of *S. typhimurium* (the type "i"flagella), inactivated flu virus and *S. typhimurium endotoxin* (LPS). Oral priming was compared to the response generated to wholly intramuscular challenge (i.m.).

Thus, the aim of these studies was to provide a method whereby the uptake of an immunogen or antigen by the gastrointestinal tract mucosa is improved to the extract that it is possible to elicit serum and secretory antibodies by oral feeding of low doses of the immunogen without the induction of oral tolerance.

Accordingly the invention describes a group of molecules (mucosal immunogens) which when fed lead to the production of serum antibodies to these proteins at comparable levels to those obtained by intramuscular injection of these molecules. Furthermore when larger quantities of these actigens are fed there is a concomitant stimulation of the production of mucosal antibodies to the immunizing molecules.

In a further aspect of this invention a process is described whereby the antibody response generated to the orally fed molecules can be augmented or changed by the co-feeding of a number of dietary molecules.

In another aspect of this invention a process is described whereby a hapten or protein can be coupled to a mucosal immunogen and the complex of which, when fed, results in the production of antibodies to the hapten or coupled protein.

| | ABBREVIATIONS | |
|---|---|---|
| 1. | Ab | Antibody |
| 2. | BSA | bovine serum albumin |
| 3. | ConA | Conconavlin A |
| 4. | DNP | dinitrophenyl |
| 5. | ELISA | Enzyme linked immunosorbent assay |
| 6. | ETEC | enterotoxigenic *E. coli* |
| 7. | GALT | gut associated lympnhoid tissue |
| 8. | HA | hydroxy apatite |
| 9. | im | intra muscular |
| 10. | LHRH | luteinizing hormone releasing hormone. |
| 11. | LPS | lipopolysaccharide |
| 12. | LT-B | neat labile toxin of enterotoxigenic *E. coli.* |
| 13. | O/N | overnight |
| 14. | per oo | oral administration |
| 15. | ps | polysaccharide |
| 16. | RT | room temperature |
| 17. | sc | subcutaneous |
| 18. | SDS-PAGE | SDS-polyacrylamide gel electrophonesis |
| 19. | TCA | trichloracetic acid. |

DISCLOSURE OF INVENTION

In a first form the invention provides a complex comprising: an immunogen; linked to a carrier molecule which is capable of specifically interacting with the mucosal epithelium of a vertebrate host; wherein both the immunological activity of the immunogen and the capacity of the carrier molecule to specifically interact with the mucosal epithelium of the vertebrate host is substantially maintained, and said complex is capable of eliciting a systemic, cellular and/or mucosal immune response in the vertebrate host.

Preferred immunogens according to the invention include:

all, part, analogues, homologues, derivatives or combinations thereof and a hormone, thereapeutic agent, antigen or hapten. These immunogens include hormones such as LHRH (luteinising hormone releasing hormone) FSH, HGH and Inhibin; allergens such as grass pollens (for instance barley and couch), weed pollens (eg. clover, dock), tree pollens (eg. ash, cyprus), plant pollens (eg. brcom), epithelia (eg. cat hair, dog hair, pig hair) and house dust, wheat chaff and Kacok; immunogens for vaccines against agents such as influenza, measles, Rubella, smallpox, yellow fever, diphtheria, tetanus, cholera, plague, typhus, BCG, haemophilus influenze, *Neisseria catarrhalis,* Kelbsiella pneumonia, pneumococci and streptococci especially *S. mutans;* and pili including pili derived from *E. Coli, N. gonorrhoeae, N. meningitis, N. catarrhalis,* Yersinia, *Pseudomonas aeruginosa,* Pseudomonas spp, *Moraxella bovis, Bacteroides nodosus,* Staphylococci spp, Streptococci spp and Bordetella spp.

Preferred carrier molecules include bacterial adhesins such as 987P, K99, CFAI, CFAII, K88 or F41; viral haemagglutinins such as from influenza, measles, Rubella, smallpox or yellow fever viruses; toxins or binding subunits thereof such as LTB ricin, abrin, diphtheria toxin, modecin, tatanus toxcin and others of similar structures; and lectins whether from plant or other origin. Lectins include for example conconavalin A, Pokeweed mitogen or lectins from *Lens culinaris, Helix pomatia, Glycine max, Arachis hypogea,* or *Ulex europeus* or Abrin, Asparagus pea, Broad bean, Camel's foot tree, Castor bean, Fava bean, Green marine algae, Hairy vetch, Horse gram, Horse shoe crab, Jack bean, Japanese wisteria, Jequirity, Scotch laburnum, Lima bean, Limulin, Lotus, European mistletoe, Mung bean, Osage orange, Pagoda tree, Garden pea, Potato, Red kidney bean, Red marine algea, Siberian pea tree, edible snail, garden snail, Spindle tree, Sweet pea, Tomato, wheat germ or winged pea.

In a preferred embodiment of the invention there is provided a complex which comprises luteinising hormone releasing hormone and LTB.

In another form the present invention provides a process for the production of a complex as described above which process comprises;

(a) reacting the immunogen with the carrier molecule to form said complex;

(b) chemically modifying the immunogen to provide at least one functional group capable of forming a chemical linkage, and reacting the immunogen and carrier molecule to form said complex; or (c) chemically modifying the carrier molecule to provide at least one functional group capable of forming a chemical linkage, and reacting the immunogen and carrier molecule to form said complex;

(d) chemically modifying the immunogen and the carrier molecule to provide functional groups capable of forming a chemical linkage, and reacting the immunogen and carrier molecule to form said complex;

(e) reacting the immunogen with at least one liking agent, and reacting the immunogen and the carrier molecule to form said complex;

(f) reacting the carrier molecule with at least one linking agent and reacting the immunogen and the carrier molecule to form said complex;

(g) reacting the immunogen and the carrier molecule with at least one linking agent, and reacting the immunogen and the carrier molecule to form said complex; or (h) a combination of any of the preceding process steps.

In another form the invention provides a process which comprises providing a recombinant DNA molecule comprising a first DNA sequence which on expression codes for the amino acid sequence of the immunogen, a second DNA sequence which on expression codes for the amino acid sequence of the carrier molecule, and vector DNA; transforming a host with said recombinant DNA molecule so that said host is capable of expressing a hybrid, proteinaceous product which comprises said complex; culturing said host to obtain said expression; and collecting said hybrid proteinaceous product.

Alternatively the invention provides a process for the production of a complex which process comprises (a) chemically synthesising the immunogen and/or the carrier molecule, and forming the complex by chemical reaction; or (b) synthesising a hybrid peptide comprising amino acid sequences of the immunogen and the carrier molecule. Preferably the peptide is prepared by solid phase, enzymatic or manual peptide synthesis.

In a preferred from of the invention the synthesised immunogen or carrier molecule whilst bound to the resin of the solid phase peptide synthesiser is coupled to the carrier molecule or immunogen respectively.

In another form of the present invention there is provided a transformant host transformed with a recombinant DNA molecule comprising a first DNA sequence which on expression codes for the amino acid sequences of all, part, an analogue, homologue, derivative or combination thereof, of the immunogen, a second DNA sequence which on expression codes for the amino acid sequence of all; part, an analogue, homolgue, derivative or combination thereof of the carrier molecule, and vector DNA.

In a preferred form of the invention the transformant host is a Gram negative or Gram positive baceterium, a yeast, fungus or a higher eukaryotic cell. In one preferred form of the invention, said host is *E. coli.* A culture of a transformant microorganism falling within the scope of the present invention had been deposited with the American type culture collection and has been designated the number:

In further form the invention provides a recombinant DNA molecule comprising a first DNA sequence which on expression codes for the amino acid sequence of the immunogen, a second DNA sequence which on expression codes for the amino acid sequence of the carrier molecule, and vector DNA. In a preferred embodiment of this form of the invention, the vector DNA is plasmid DNA but alternative vectors are envisaged within the scope of the present invention and these include viruses, bacteriophages and cosmids. In one preferred form of the invention there is provided plasmid pBTAK66 which when a host cell is transformed with said plasmid will yield a proteinceous product which includes a polypeptide falling with the scope of the present invention.

In a further form of the invention there is provided a polynucleotide sequence which comprises a first hybrid polynucleotide sequence which acts as a coding sequence for a fusion product comprising an amino acid sequence of an immunogen fused to an amino acid sequence of a carrier molecule, a polynucleotide sequence sufficiently related to said first hybrid polynucleotide sequence so as to hybridize to said first hybrid polynucleotide sequence, a polynucleotide sequence related by mutation, including single or multiple base substitutions, deletions, insertions and inversions, to said first hybrid polynucleotide sequence or hybridizing sequence or a polynucleotide sequence which on expression codes for a polypeptide which deplays similar biological or immunological activity to said fusion product.

Preferably the polynucleotide sequence is one wherein the first hybrid polynucleotide sequence acts as a coding sequence for the amino acid sequence of all, part, an analogue, homologue, derivative or combination thereof of LHRH fused to the amino acid sequence of a carrier molecule, more preferably LTB.

In a further form of the invention there is provided a medicament which comprises a complex according to the invention together with a pharmaceutically acceptable carrier or diluent. Examples of pharmaceutically acceptable carriers and diluents include typical carriers and diluents such as tablets, aquecs solutions, sodium bicarbonate solutions and similar diluents which neutralise stomach acid or have similar buffering capacity, glycols, oils, oil-in-water or water-in-oil emulsions, and include medicaments in the form of emulsions, gels, pastes and viscous colloidal dispersions. The medicament may be presented in capsule, tablet, slow release or elixir form or as a gel or paste or may be presented as a nasal spray and in this form may be in the presence of an aerosol. Furthermore, the medicament may be provided as a live stock feed or as food suitable for human consumption.

The present inventors have also found that co-administration of certain dietary molecules with a complex of the present invention can selectively modulate the magnitude and/or type of the immune response to the immunogen of the complex.

Accordingly the present invention further provides a medicament which comprises the complex of the present invention together with a dietary molecule which dietary molecule can selectively modulate the magnitude and/or type of the immune response to the immunogen of the complex.

The dietary molecule envisaged by the present invention include basic, neutral and acidic amino acids, such as argenine, histidine, lysine, alanine, cysteine, cystine, glycine, isoleucine, leucine, methionine, phenylalanine, proline, serine, threonine, tryptophan, tyrosine, valine, aspartic acid, glutamic acid; water soluble and insoluble vitamins, such as thiamine, riboflavin, pyridoxal, cyanocobalamin ($V.B_{12}$) ascorbic acid (V.C). Vit $D_2$, etc—Ergosterol, Vit.E, Vit.A, Vit K etc; sugars including monosaccharides e.g. galactose, mannose, mannitol, sorbitol, glucose, xylose, Allose, altrose, arabinose, digitoxose, arythrose, fructose, lyxose, muramic acid, mannose, pyruvic acid, ribose, tagatose, talose and the amidatec and N acetylated, derivatives thereof; oligosaccharides e.g. lactose, maltose, melibiose, sucrose, cellubiose, N,N diacetyl chitoblose, gentobiose, isomaltose, lactobionic acid, trehalose, turanose; and dietary minerals and co-factors such as manganese, magnesium, zinc, calcium and iron.

The invention also provides a method of presenting a complex of the present invention which method comprises the mucosal administration of a complex of the present invention together with a dietary molecule capable of modulating the magnitude and/or type of immune response of the immunogen.

The invention also provides the oral administration of the medicaments of the invention, in order to elicit a response to the active molecule in the host. Such a response, in the case where the active molecule is an antigen or hapten may be a systemic and/or a mucosal immune response. In the case where the active molecule is LHRH or a derivative, analogue, homologue, part or combination thereof, of LHRH, the response will be inhibition of gonadal function in the host. Where the oral medicament incorporates a dietary molecule according to the invention, the invention provides a method for enhancing the host's response to the active molecule which comprises administering such an oral medicament to the host.

BRIEF DESCRIPTION OF THE DRAWINGS

FIG. 1 (SEQ ID NOS 8–12, respectively) shows the N-terminal amino acid sequence of the 987P pilin subunit, in comparison with the N-terminal amino acid sequence of other pilin proteins.

MODES FOR CARRYING OUT THE INVENTION

Materials

Lectins were purchased from Sigma Chemical Co. Inactivated flu vaccine was purchased from the Commonwealth Serum Labs. (Australia). Sugars and vitamins were obtained from the following sources:—Lactose (AR grade)—Ajax Chemicals, Sydney, Australia; Fructose D(-), Mannose D(+). Sorbitol and Xylose D(+) (all AR grade)—B.D.H. Chemicals Ltd. Poole, England; Melibiose D(+)—Sigma Chemical Co., St. Louis, Miss.; Retinal (Vit A. aldehyde)—Fluka AG, Chemicals Fabrik Buchs, Switzerland; Thiamine—HCl (Vit B1), Riboflavin (Vit B2), Pyridoxal (Vit B6), Cyanocobalomin (Vit B12), L-ascorbic acid (Vit C), Ergosterol (Pro Vit D) and D1-a-tocopherol (Vit E)—Sigma Chemical Co., St. Louis, Miss.

Bacterial Strains and Media

The *E. coli* K99, 987P and LTB strins used in these experiments are listed in Table 1, and were the generous gifts of Dr. Susan Clark, (Molecular Biology Laboratory Biotechnology Australia). Cultures were grown at 37C (unless otherwise specified) with shaking in Luria broth (LB) with or without 1 mM isopropylthio-n-D-galactopyranoside (IPTG) as indicated (Table 1). Salmonella typhimurium was grown at 37C with shaking in LB plus 0.2% glycerol.

TABLE 1

| Stain | Genetic Marker | Strain Origin | Phenotype |
| --- | --- | --- | --- |
| BTA 595 | p BTA 193 | RB 791 | LTB + |
| BTA 604 | p BTA 201 | MC 1061 | 987P |
| BTA 262 | p BTA 106 | ED 8654 | K99 |

+ Included c̃ 1 mM IPTG

PURIFICATION OF ANTIGENS

Pili Preparation

*E. coli* expressing the cloned pili, as detected using radiolabelled antiserum were harvested during logarithmic phase of growth. Cultures were heated at 60C for 30 minutes, after which the organisms were pelleted by centrifugation (3,000×g, 30 min 4C). The supernatant was examined for pili content by 12.5% SDS-PAGE using a modification of the method of Laemmli (Laemmli, 1970; Salit eta al., 1980).

K99 purification:—The culture supernatant was adjusted to pH 9.7 with (lON NaOH and stirred at room temperature (R.T.) for 10 minutes. The resultant precipitate containing pili was recovered by centrifugation (3,000×g, 30 min 4C) and resuspended in 100 ml distilled $H_2O$ ($dH_2O$) ph 7.2. This procedure was repeated twice.

987P Purification:—Procedures used were as detailed above except that pili precipitation was achieved by adjusting the pH to 3.9 with glacial acetic acid.

Hydroxyapatite Chromatography

Hydroxyapatite (HA) (DNA grade Bio-Gel HTP, Bio-Rad) was gently swollen in an excess of $dH_2O$ and after a brief period ($<$2 min.), fines were decanted gently. Fresh $dH_2O$ was added and used to gently resuspend the gel after which fines were decanted again. This procedure was repeated several times. A column (30×5 cm) was filled with slurry of approximately 30% HA and allowed to settle by gravity. Tight packing was then achieved by passing $dH_2O$ through the column at a flow rate of 16 ml/hr until the gel bed surface was stationary. Samples (100 ml) of either K99 or 987P were applied at flow rates not exceeding 30 ml per hour. The column was than washed with $dH_2O$ until no protein was detected in the flow through as detected at 280 nm. Pili were eluted at a flow rate of 30 ml/hr using a linear gradient of 15 to 250 mM sodium phosphate ph 7.5. Fractions were collected and examined by SDS-PAGE. The pili peak was recovered and pooled.

Ion-exchange Chromatography

Pooled fractions of K99 and 987P pili (from the HA chromatography) were reprecipitated with NaOH (pH 9.7) or glacial acetic acid (pH 3.9)repsectively. After centrifugation (3.000<g, 10 min), the pellets containing pill were resuspended in 50 mM Citrate buffer, pH 5.5 (K99) and 50 mM Tris.HCl ph 8.5 (987P) prior to loading on the ion-exchange columns equilibrated with the same buffers. K99 and 987P were located onto CM and DEAE columns respectively at a flow rate of 100 ml/hr, washed with 2 volumes of loading buffer and the pili eluted using a linear gradiient from 10 mM to 0.5 M NaCl in the aquilibration buffers. Fractions were examined by SDS-PAGE for protein content and LPS contamination, according to the method of Tsai and Frasch (1982).

LTB Purification

Three litres of LTB supernatant was diluted to 6l with $dH_2O$. The pH was adjusted to 6.5 with glacial acetic acid and loaded onto a 5×30 cm column of fastflow CM-Sepharose equilibrated with 10 mM phosphate buffer pH 6.5 at a flow rate of 1.2 l/hr. The column was then washed with 400 mls of 10 mM phosphate buffer pH 6.5 and bound protein aluted with a linear gradient of 10–500 mM Nacl in 10 mM phosphate pH 6.5 Fractions were collected and analysed by SDS-PAGE, the LTB peak was pooled.

Flagellae Isolation

Late log phase cultures of bacteria were pelleted by centrifugation (3,000×g for 15 mins. at 4C). The cells were resuspended in saline and heated at 60C for 30 minutes, followed by centrifugation (3000×g, 10 min 4° C.). The supernatant was precipitated by adding a solution of 100% TCA (w/v) to give a final concentration of 10% (w/v) and spun for 10 min at 1,500×g 4C. The pellet was resuspended in a small volume of 1 M Tris ph 8.8 and sonicated until in solution. Ethanol was added to a final concentration of 80% (v/v) and the flagellae spun down at 2,000<g, 10 min at 4C. The pellet was resuspended in acetone, sonicated into suspension and reprecipitated by centrifugation (5,000×g). Finally the pellet was brought into solution by boiling in 10% SDS and 50 mM EDTA in 10 mM Tris. HCl ph 8.0 prior to Sephacryl S-200 chromatorgraphy.

Flagellae Purification

After boiling for 15 min the flagellae were clarified by centrifugation for 5 min. In a Beckman benchtop microfuge to remove non-solubilized material. The supernatant was applied to a 2.5×80 cm column of Sephacryl—S200 (Pharmacia, Fine Chemicals) equilibrated with 20 mM Tris pH 8.8, 0.1% SDS and 10 mM EDTA and eluted using the same buffer. Fractions were collected and analysed by SDS-PAGE. Finally the flagellae peak was pooled and precipitated with 10% (final conc.) TCA followed by centrifugation, ethanol and acetone washes as described previously. The final pellet was resuspended in $dH_2O$.

Lipoolysaccharide (LPS) Purification

Overnight cultures of *S. typhimurium* were extracted (30 min R. Temp) with 0.5 M $CaCl_2$ in 20% ethanol (v/v) containing 100 mM citrate pH 3.0 and 5% Zwittergent 3.12 (w/v) (Calbiochem.). Bacteria were pelleted by centrifugation (3,000×g, 10 min at 4C) and the pellet resuspended in 50 mM EDTA pH 8.0 The suspension was stirred vigorously for 30 min at R. temp. After removal of the bacteria by centrifugation ethanol was added to the supernatant to a final concentration of 75%. Protein material was pelleted and the supernatant adjusted to 90% ethanol. The precipitate which formed was pelleted and washed with acetone, reprecipitated and finally resuspended in $dH_2O$. The preparation was assayed for sugar content using the Anthrone reagent (Herbert et al, 1985) and checked for the presence of contaminating proteins using SDS-PAGE. Commercial *E. coli* LPS (Sigma Chemical Co.,) was used as a standard in both assays. Gels were stained for LPS using a silver stain according to the method of Tsai and Frasch (1982).

Preparation of Polysaccharide (PS)

Lipid A was cleaved from the *S. typhimunium* LPS preparation by incubating the LPS with 1 M glacial acetic acid and heating at 100C for 2–5 hrs. Lipid A was then removed by centrifugation at 3,000×g for 10 mins at 4C.

Description of Purified Antigens

SDS-PAGE analysis of purified K99 and 987P pili preparations revealed the presence of a single band migrating at 17,500 and 20,000 mol. wt. (respectively) under reducing conditions (FIG. 1). This agrees with the published data of Isaacson and others (Isaacson & Richter, 1981; Morris et al. 1980; de Graaf et al. 1981; Fusco et al, 1978). The ease of precipitation of these proteins at pH 9.7 and 3.9 (for K99 and 987P, respectively) suggests that the pI of these two proteins to be around these ranged (see:—Isaacson & Richter, 1981; de Graaf et al, 1981). Silver staining of these preparations showed them to contain little ($<$1 µg/100 µg protein) or no contamination with LPS.

Determination of the 987P Amino Terminal Sequence

Amino terminal micro-sequencing was perfored for us by Biotechnology Research Enterprises S.A. Ltd. Adelaide, South Australia. A 100 nmole sample of 987P purified as described above was assayed. The amino terminal sequence of 987P is compared with the published sequence of K99 and reveals no homology between these two molecules (FIG. 1) (Gaastra and de Graaf, 1982).

Purified LTB, and *S. typhimurium* flagellae were also found to be free of contaminating LPS and to travel as monomers of apparent molecular weights of 12,500 and 52,000 respectively when examined by SDS-PAGE under reducing conditions.

Silver stained SDS-PAGE gels of purified LPS revealed no detectable protein contamination. Complex sugar content, as assayed by Anthrone reaction, was found to be 2 mg/ml. Lipid A free polysaccharide was also found to contain 2 mg/ml polysaccharide and it's failure to move on SDS-PAGE (as revealed in the silver stained gels) showed it to be free of contaminating lipid.

Dinitrophenylation of Antigens

K99, LTB and lectins were dintrophenylated according to the method of Little and Elsen (1967). Briefly, carriers (in 0.1 M carb/bicarb buffer pH 9.5) were reacted with a 0.1 M solution of DNFB (in Acetone) overnight at R.T. The proteins were then dialysed extensively against the coupling buffer. Previous studies by us have shown that 987P has no free amino groups exposed for coupling so a diamino spacer was first linked to the free carboxyl moieties of the protein as follows: 10 mg or purified 987P was precipitated at pH 3.9 by the addition of glacial acetic acid. The pill were removed by centrifugation at 3,000×g, 10 min at 4C. The pellet was resuspended in dH$_2$O and the pH raised to 6.5 with IN NaOH. The pili solution was then reacted with 1-ethyl-3-(3-Dimethylaminopropyl) carbodiimide-HCL (EDAC, Bio Rad Laboratories, Richmond, Calif.), to a final concentration of 0.5 mM in the presence of 20 mM 1,2-diaminoethane (BDH Chemicals Ltd. Poole, England), overnight at room temperature (20–23C). The amino-substituted 987P was dialysed for 24 hrs against two changes of 0.1 M carbonate/bicarbonate buffer pH 9.5 before being used in the subsequent conjugation steps. Lectin binding sites were protected during their reaction with DNFB by the addition of the Lectin specific sugars. Thus, 50 mM solutions of D-glucose, D-mannose, D-glucose, N-acetyl-D-galactosamine, D-galactose, N-acetyl-D-galactosamine, D-gal(1-3)-D-galN-Ac, and L-fucose, were added to the following lectins:—Conconavlin A, Pokeweed mitogen, Lens culinaris, Helix pomatia, Phaseolus vulgaris Glycine max, Arachis hypogea and Ulex eruopeus, respectively.

Antigens Administration

Female C57BL/6J mice (18–22 gm) were obtained from the Aminal Resources Centre Perth, Wester Australia). All mice were starved for 3–4 hours prior to oral or intramuscular (i.m.) administration of antigens. Mice were fed antigen at appropriate concentrations in 0.5 ml of 0.1M carb/bicarbonate buffer pH 9.5 using a specially prepared feeding needle. Parallel doses of antigen were injected i.m., in 0.1 ml or sterile physiological saline, into the left hind leg. Groups of 5 mice receiving antigen either orally or im were given two identical doses of antigen, on day 0 and day 14. A blood sample was taken approx. 0.5 ml) from the retro orbital plexus on day 14 and day 21. Mice were then sacrificed by cervical dislocation and gut washes performed on the small intestine in the following manner. The small intestine was carefully removed and a small quantity of washing buffer (1.0 ml, 30 mM Tris·HCl pH 8.8, 0.9% NaCl, 50 mM EDTA plus 1.0% Tween 20) introduced into the lumen of the gut via a blunt ended feeding needle. After gently <neading the intestine the contents were squeezed out through forefinger and thumb. Gut washes so obtained were immediately centrifuged to remove debris and stored at −20C until assayed. Blood samples were allowed to clot at 4C before removal of the serum and storage at −20.

Enzyme Linked Immunosorbent Assay (ELISA)

The ELISA for the determination of antibody titres was performed as described previously by Russell-Jones et al., (1984).

EXAMPLE 1

Identification of Molecules Active as Mucosal Immunogens

The possible potential of a number of molecules known to possess the capacity to bind to the intestinal mucosa and to stimulate the production of an immune response after oral administration of these molecules was examined. The response generated by these molecules was compared to the response seen after similar feeding of other molecules having no mucosal binding functions.

As seen in Table 1.1, three broad classes of proteins were detected in these experiments:—those that elicited a serum and intestinal response, K99, 987P, LTB, flu vaccine and the various lectins (Class 1) (these shall henceforth be referred to as mucosal immunogens), those that elicited only a serum response (LPS) (Class II) and those that failed to elicit either a serum or intestinal response at the doses tested (Flagellae, BSA and P.S.) (Class III). Within class I antigens 987P was a significantly superior stimulator of IgA antibody (ab) (48.5±1.8) when compared to LTB (12.2±4.4), or K99 (3.2±4.9). In addition 987P also stimulated gastrointestinal IgG (10.8±1.76) to a greater extent than either K99 (3.0±5.3), or LTB (1.0), and only 987P was capable of stimulating serum IgA (10.8±8.8). All four class I antigens stimulated serum IgG to similar degrees (Table 1.1). The class II antigen, LPS, stimulated a small serum IgG response (12.1±1.0) with no concomitant IgA or agastrointestinal reactivity. Finally BSA, flagellae and the polysaccharide moeity of LPS—class III antigens—failed to induce either serum or intestinal IgG or IgA. Representative samples from all three classes: K99, 987P, LTB, LPS and flagellae were administered intramuscularly and screened for both serum and intestinal response (Table 1.2). Class I and II antigens gave similar serum IgG responses yet failed to produce serum IgA or Intestinal IgG/IgA Ab responses. Only the anti-LPS serum IgG response appeared significantly improved by i.m. immunisation. Each of 987P, K99 and LTB were further examined in dose response studies after both oral and i.m. administration. As seen in Tables 1.3 and 1.4, 987P yielded consistently higher titers than either K99 or LTB regardless of the route of administration. Interestingly the class I antigen—LTB—displayed a bell shaped dose-response with a plateau maximum between 10 and 50 µg. None of the other class I antigens produced this effect, nor die the LTB when administered 1 m. Oral administration of all class I antigens (Ag) elicited higher levels of intestinal IgA Ab (S-IgA) over the broad range of doses tested. Comparison between the two routes of administration suggests that although i.m. injection consistently gave higher titers, oral administration of mucosal immunogens resulted in comparable levels of antibody production to that obtained by the i.m. route between 10 and 100 µg of antigen for class I and II antigens.

TABLE 1.1

Immune reactions to orally presented antigens

| Antigen used for immunisation (20 μg does) | Immune response,* day 21. | | | |
|---|---|---|---|---|
| | Serum | | Intestinal | |
| | IgG | IgA | IgG | IgA |
| K99 | 968 ± 120 | <4 | 3.0 ± 5.2 | 3.2 ± 4.9 |
| 987P | 776 ± 64 | 10.8 ± 8.8 | 10.9 ± 1.7 | 48.5 ± 4.88 |
| LTB | 1351 ± 211 | <4 | <4 | 12.2 ± 4.4 |
| Flue vac | 179 ± 34 | <4 | <4 | <4 |
| Flagellae | <4 | <4 | <4 | <4 |
| LPS | 12.1 ± 1.0 | <4 | <4 | <4 |
| PS | <4 | <4 | <4 | <4 |
| BSA | <4 | <4 | <4 | <4 |
| Con A** | 666 ± 84 | <4 | nd | nd |
| FW-mitogen** | 641 ± 119 | <4 | nd | nd |
| L. culinaris** | 954 ± 48 | <4 | nd | nd |
| H. pomatia** | 591 ± 127 | <4 | nd | nd |
| P. vulgaris** | 1378 ± 110 | 4.8 ± 2.3 | nd | nd |
| G. max** | 1529 ± 65 | 3.1 ± 6.9 | nd | nd |
| A. hypogea** | 1276 ± 242 | <4 | nd | nd |
| U. europeus** | 1583 ± 94 | <4 | nd | nd |

*The reciprocal of the antiserum dilution that gave an ELISA reading of 0.5 after 45 minutes at 37 C. Each value represents one mean value obtained from 5 mice ± 1 standard deviation.
**Each lectin was substituted with 4 DNP molecules/mole lectin. The ELISA titre represents the anti DNP response as measured against DNP-BSA.

TABLE 1.2

Immune reactions to antigens presented intramuscularly

| Antigen used for immunisation (20 μg does) | Immune response,* day 21 | | | |
|---|---|---|---|---|
| | Serum | | Intestinal | |
| | IgG | IgA | IgG | IgA |
| K99 | 1024 ± 94 | <4 | <4 | <4 |
| 987P | 1552 ± 112 | <4 | <4 | <4 |
| LTB | 1782 ± 100 | <4 | <4 | <4 |
| Flagellae | 1595 ± 227 | <4 | <4 | <4 |
| LPS | 388 ± 58 | <4 | <4 | <4 |

*See Table 1.1

TABLE 1.3

Dose response to orally presented antigens

| Antigen | Immune response*, day 21, per dose (μg) | | | | | |
|---|---|---|---|---|---|---|
| | 0.1 | 1.0 | 10 | 50 | 100 | 1,000 |
| Serum IgG | | | | | | |
| K99 | 1.0 | 4.0 | 28 | 675 | 1351 | 4096 |
| 987P | 4.0 | 14 | 84 | 588 | 1024 | 3104 |
| LTB | 9.0 | 194 | 1351 | 1331 | 891 | 891 |
| Serum IgA | | | | | | |
| K99 | <4 | <4 | <4 | <4 | <4 | <4 |
| 987P | <4 | <4 | <4 | 9.6 | 18.3 | 32 |
| LTB | <4 | <4 | <4 | <4 | <4 | <4 |
| Intestinal IgG | | | | | | |
| K99 | <4 | <4 | <4 | <4 | <4 | <4 |
| 987P | <4 | <4 | <4 | 4.0 | 4.0 | 8.0 |
| LTB | <4 | <4 | <4 | <4 | <4 | <4 |
| Intestinal IgA | | | | | | |
| K99 | <4 | <4 | <4 | 4.0 | 16.7 | 87 |
| 987P | <4 | <4 | 9.1 | 54 | 84 | 147 |
| LTB | <4 | <4 | <4 | 4.0 | 4.0 | 8.0 |

*See Table 1.1.

TABLE 1.4

Dose response to intramuscularly presented antigens

| Antigen | Immune response*, day 21, per dose (μg) | | | | | |
|---|---|---|---|---|---|---|
| | 0.1 | 1.0 | 10 | 50 | 100 | 1,000 |
| Serum IgG | | | | | | |
| K99 | 256 | 445 | 776 | 1351 | 1776 | 5104 |
| 987P | 256 | 891 | 1024 | 3104 | 4096 | 18820 |
| LTB | 64 | 588 | 1176 | 2702 | 4096 | 8192 |
| Serum IgA | | | | | | |
| TK99 | <4 | <4 | <4 | <4 | <4 | <4 |
| 987P | <4 | <4 | <4 | <4 | <4 | <4 |
| LTB | <4 | <4 | <4 | <4 | <4 | <4 |
| Intestinal IgG | | | | | | |
| K99 | <4 | <4 | <4 | <4 | <4 | <4 |
| 987P | <4 | <4 | <4 | <4 | <4 | <4 |
| LTB | <4 | <4 | <4 | <4 | 7.0 | 16 |
| Intestinal IgA | | | | | | |
| K99 | <4 | <4 | <4 | <4 | <4 | 4.6 |
| 987P | <4 | <4 | <4 | <4 | 4.0 | 6.0 |
| LTB | <4 | <4 | <4 | <4 | 16.0 | 11.1 |

*See Table 1.1.

EXAMPLE 2

Effect of dietary molecules on the immune response to mucosal immunogens upon oral presentation.

Initial studies in our laboratory using outbred Swiss male mice suggested that it was possible to alter the immune response to orally presented antigens by the co-feeding of certain dietary molecules. Accordingly, the mucosal immunogens, K99, 987P and LTB were fed to mice in the presence of a mumber dietary sugars and vitamins. It was reasoned that as the different antigens were known to bind to different molecules on the surface of the intestinal epithelium, and as it is known that there is a change in the distribution of glycoproteins and glycolipids throughout the length of the gut as well as a change in distribution of absorptive cells, it might be possible to stimulate the uptake of molecules bound to these cells by presenting the antigens in the presence of the specific dietary molecule normally taken up by these cells. An extension to this argument would be that the profile of stimulatory molecules would change from antigen to antigen.

The results represented in Tables 2.1, 2.2 and 2.3 demonstrate that although most of the vitamins and sugars have had some effect in modulating the immune response to K99, 987P and LTB, some dietary molecules appear to be selective as to which mucosal immunogen they appeared to influence but also as to whether they induced primarily a secretary or serum response. Thus, the serum antibody response to K99 was significantly increased ($P<0.05$) by co-administration with Vit B12 of Melibiose, unchanged when given with Vit B2, Vit D, Vit E, Fructose or Mannose and decreased to varying extents with Vit A, Vit B1, Vit B6, Vit C, Lactose, Sorbitol and Xylose (Table 2.1).

In contrast, the serum Ab response to oral 987P (Table 2.2) was elevated when 987P was co-administered with Vit B6, Vit B12, Vit C, Vit E, Fructose or Mannose, it was unchanged with Vit A, Vit B1, Vit B2, Lactose, Melibiose, Sorbitol and Xylose, and decreased in the presence of Vit D. LTB on the otherhand, displayed a unique profile for the effect of co-feeding of dietary molecules on the serum Ab levels. The results in Table 2.3 clearly show an augmented serum titer to LTB in the presence of Vit A, Vit B2, Vit D, Fructose, Mannose and Xylose. Little or no change with Vit B1, Vit B12, Vit C or Melibiose and almost complete inhibition with Vit B6, Vit E, Lactose, Melibiose and Sorbitol. The inhibition of an immune response seen with Vit B6, Lactose, Melibiose and Sorbitol is to be expected due to the similarities in structure of these compounds to Galactose which is claimed to be the specific sugar determinant on the GM1 ganglioside to which LTB is known to bind. These results are broadly suggestive that K99, 987P and LTB bind to and are internalized by discreet cells of the microvillous epithelium.

Dose response experiments (Tables 2.4, 2.5 and 2.6) demonstrate that is possible to stimulate the secretary arm of the immune system without concomitant stimulation of serum antibodies, or conversely to augment the serum response without affecting the level of secretary Abs, by the simple addition of dietary molecules to the orally presented mucosal immunogens. Thus cofeeding of large doses of Vit B12 or melibiose with K99 leads to a two to eightfold (respectively) increase in serum Ab with little concomitant increase in secretory Abs. Conversely cofeeding of Vit D in increasing doses lead to a drop in serum Abs and a rise in secretory Ab. Certain dietary molecules on the other hand also result in stimulation of both secretory and serum Ab titres as shown by an eightfold increase in serum Ab and a 1000 fold increase in S-IgA upon cofeeding of Vit C with 987P.

Experiments in which the mucosal immunogens were injected i.m. together with vitamins or sugars showed little effect if any on the immune response thus demonstrating that the change in response due to cofeeding of these molecules with the mucosal immunogens must occur on or near the site of absorption of these molecules rather than directly upon the immune system (Table 2.7).

TABLE 2.1

Effects of dietary molecules on the immune response to orally administered K99 (20 µg)*

| Dietary Molecule | Dose | Antibody Response | | | |
|---|---|---|---|---|---|
| | | Serum | | Intestinal | |
| | | IgG | IgA | IgG | IgA |
| none | — | 968 ± 120 | <4 | 3.0 ± 5.2 | 3.2 ± 4.9 |
| Vit A | 20 µg | 278 ± 184 | 3.4 ± 4.7 | 1.5 ± 1.1 | 5.4 ± 3.0 |
| Vit B1 | " | 117 ± 107 | 1.5 ± 2.0 | 2.7 ± 1.0 | 2.1 ± 0.9 |
| Vit B2 | " | 604 ± 216 | <4 | 2.3 ± 1.7 | 2.0 ± 0.6 |
| Vit B6 | " | 14 ± 50 | <4 | 2.0 ± 1.5 | 3.5 ± 8.2 |
| Vit B12** | " | 3377 ± 1266 | 4.0 ± 3.0 | <4 | <4 |
| Vit C** | " | 318 ± 255 | 2.0 ± 2.8 | 32 ± 1.1 | 98 ± 70 |
| Vit D** | " | 1921 ± 640 | <4 | <4 | 6.3 ± 2.7 |
| Vit E | " | 512 ± 128 | <4 | <4 | 4.4 ± 2.1 |
| Fructose | 50 mM | 1782 ± 966 | 8.4 ± 3.7 | 2.9 ± 1.6 | 34.7 ± 14.2 |
| Lactose | " | 84 ± 204 | <4 | <4 | 22.9 ± 6.7 |
| Mannose | " | 1176 ± 411 | 2.6 ± 3.4 | 10.2 ± 3.4 | 21.1 ± 40.3 |
| Meliboise** | " | 1840 ± 208 | 1.2 ± 1.4 | 3.2 ± 2.0 | 4.4 ± 3.7 |
| Sorbitol | " | 77 ± 179 | <4 | 1.3 ± 0.4 | 20.5 ± 3.4 |
| Xylose | " | 328 ± 217 | <4 | 1.9 ± 1.1 | 2.8 ± 1.3 |

*The reciprocal of the antiserum dilution that gave an ELISA reading of 0.5 after 45 min at 37° C. on day 21 after immunisation. Each value is the mean of five mice ± 1 standard deviation.
**Each value is the mean of 15 mice ± 1 standard deviation. These molecules were also tested in dose response experiments.

TABLE 2.2

Effects of dietary molecules on the immune response to oral 987P (20 µg)*

| Dietary Molecule | Dose | Antibody Response | | | |
|---|---|---|---|---|---|
| | | Serum | | Intestinal | |
| | | IgG | IgA | IgG | IgA |
| none | — | 776 ± 64 | 10.8 ± 8.8 | 10.9 ± 1.7 | 48.5 ± 1.8 |
| Vit A** | 20 µg | 648 ± 40 | 29.0 ± 20 | 8.4 ± 3.1 | 20.5 ± 24.6 |
| Vit B1 | " | 891 ± 127 | 12.1 ± 3.6 | 9.4 ± 1.5 | 14.7 ± 6.5 |
| Vit B2 | " | 1082 ± 271 | 31.1 ± 11.9 | 17.8 ± 7.6 | 21.1 ± 11.9 |
| Vit B6 | " | 1782 ± 509 | 23.6 ± 8.7 | 32.8 ± 9.3 | 39.9 ± 7.1 |

TABLE 2.2-continued

Effects of dietary molecules on the immune response to oral 987P (20 μg)*

| Dietary | | Antibody Response | | | |
|---|---|---|---|---|---|
| | | Serum | | Intestinal | |
| Molecule | Dose | IgG | IgA | IgG | IgA |
| Vit B12 | " | 3983 ± 1307 | 48.5 ± 16.0 | 35.7 ± 3.4 | 91.7 ± 31.9 |
| Vit C** | " | 4521 ± 1046 | 54.2 ± 19.2 | 10.8 ± 6.9 | 84.1 ± 14.3 |
| Vit D** | " | 398 ± 89 | 18.8 ± 11.0 | 13.1 ± 4.9 | 34.7 ± 8.1 |
| Vit E | " | 3468 ± 776 | 9.18 ± 2.6 | 11.1 ± 4.2 | 19.9 ± 3.9 |
| Fructose | 50 mM | 2048 ± 894 | 10.8 ± 3.6 | 15.1 ± 4.7 | 23.5 ± 3.2 |
| Lactose | " | 1128 ± 662 | 15.3 ± 2.9 | 19.6 ± 2.5 | 21.7 ± 6.1 |
| Mannose | " | 4970 ± 2270 | 24.9 ± 11.7 | 14.3 ± 1.9 | 16.9 ± 26.4 |
| Melibiose** | " | 1243 ± 474 | 30.3 ± 7.7 | 91.7 ± 10.9 | 124.5 ± 22.6 |
| Sorbitol** | " | 1389 ± 307 | 38.8 ± 19.1 | 22.9 ± 4.6 | 91.7 ± 18.6 |
| Xylose | " | 1024 ± 941 | 6.2 ± 1.9 | 19.6 ± 7.1 | 21.4 ± 5.4 |

*See Table 2.1
**See Table 2.1

TABLE 2.3

Effects of dietary molecules on the immune response to oral LTB (20 μg)*

| Dietary | | Antibody Response | | | |
|---|---|---|---|---|---|
| | | Serum | | Intestinal | |
| Molecule | Dose | IgG | IgA | IgG | IgA |
| none | — | 1351 ± 211 | <4 | <4 | 12.2 ± 4.4 |
| Vit A | 20 μg | 4705 ± 676 | <4 | <4 | 21.1 ± 7.5 |
| Vit B1 | " | 1782 ± 309 | <4 | <4 | 16.0 ± 2.1 |
| Vit B2 | " | 3565 ± 908 | <4 | <4 | 16.0 ± 3.7 |
| Vit B6** | " | 9.18 ± 1.1 | <4 | <4 | <4 |
| Vit B12 | " | 1024 ± 116 | <4 | <4 | 24.2 ± 11.9 |
| Vit C | " | 337 ± 206 | <4 | <4 | 16.1 ± 5.0 |
| Vit D | " | 4097 ± 74 | <4 | <4 | 13.9 ± 2.2 |
| Vit E | " | 194 ± 64 | <4 | <4 | 18.4 ± 3.6 |
| Fructose | 50 mM | 6208 ± 1192 | <4 | <4 | 10.5 ± 3.3 |
| Lactose** | " | 5.0 ± 1.0 | <4 | <4 | <4 |
| Mannose | " | 4096 ± 658 | <4 | <4 | 24.2 ± 8.1 |
| Melibiose | " | 512 ± 76 | <4 | <4 | 8.0 ± 4.0 |
| Sorbitol** | " | 8.0 ± 1.2 | <4 | <4 | <4 |
| Xylose | " | 5404 ± 2211 | <4 | <4 | 21.1 ± 9.2 |

*See Table 2.1
**See Table 2.1

TABLE 2.4

Effect of orally administered dietary molecules on the Immune response to oral antigen (K99)*

| Dietary | Day 21 Immune response per dose (μg~, mM+) | | | | | | |
|---|---|---|---|---|---|---|---|
| Molecule | 0.1 | 1.0 | 10 | 50 | 100 | 500 | 1000 |
| Serum IgG | | | | | | | |
| Vit B12 | 256 | 675 | 1176 | 1552 | 2352 | nd | 2352 |
| Vit C | 512 | 891 | 588 | 675 | 1024 | nd | 891 |
| Vit D | 588 | 588 | 776 | 891 | 1782 | nd | 891 |
| Melibiose | 128 | 256 | 675 | 4096 | 9410 | 256 | nd |
| Serum IgA | | | | | | | |
| Vit B12 | <4 | <4 | 4.0 | 5.2 | <4 | nd | <4 |
| Vit C | <4 | <4 | 4.0 | 16.0 | 16.0 | nd | 16.0 |
| Vit D | <4 | <4 | <4 | <4 | <4 | nd | <4 |
| Melibiose | <4 | <4 | <4 | 4.0 | 4.0 | 4.0 | nd |
| Intestinal IgG | | | | | | | |
| Vit B12 | <4 | <4 | <4 | <4 | <4 | nd | <4 |
| Vit C | <4 | 4.0 | 16.2 | 32.0 | 36.1 | nd | 38.0 |
| Vit D | <4 | <4 | <4 | <4 | <4 | nd | <4 |
| Melibiose | <4 | <4 | <4 | 4.0 | 4.0 | 4.5 | nd |
| Intestinal IgA | | | | | | | |
| Vit B12 | <4 | <4 | <4 | <4 | 5.2 | nd | 13.9 |
| Vit C | <4 | <4 | 4.0 | 16.0 | 36.7 | nd | 73.5 |
| Vit D | <4 | <4 | 4.0 | 8.0 | 13.9 | nd | 24.2 |
| Melibiose | 5.2 | 4.0 | 4.0 | 4.0 | 9.2 | 4.0 | nd |

~, dose in μg, vitamins: +, dose in mM, sugars.
*See Table 2.1

TABLE 2.5

Effect of orally administered dietary molecules on the immune response to oral antigen (987P)

| Dietary molecule | Day 21 Immune response per dose ($\mu$~,mM+) | | | | | | |
|---|---|---|---|---|---|---|---|
| | 0.1 | 1.0 | 10 | 50 | 100 | 500 | 1000 |
| Serum IgG | | | | | | | |
| Vit A | 512 | 675 | 388 | 891 | 675 | nd | 588 |
| Vit C | 891 | 1351 | 4096 | 8192 | 8192 | nd | 9410 |
| Vit D | 2352 | 2048 | 256 | 73 | 147 | nd | 1351 |
| Meliboise | 512 | 481 | 463 | 1250 | 1006 | 1292 | nd |
| Sorbitol | 873 | 1133 | 1024 | 1400 | 2123 | 85 | nd |
| Serum IgA | | | | | | | |
| Vit A | <4 | <4 | 16.0 | 30.0 | 36.0 | nd | 64.0 |
| Vit C | 4.0 | 4.0 | 32.0 | 66.0 | 73.1 | nd | 86.7 |
| Vit D | 64 | 16.0 | 16.0 | 16.0 | 28.0 | nd | 38.1 |
| Miliboise | nd | nd | nd | nd | nd | nd | nd |
| Sorbitol | nd | nd | nd | nd | nd | nd | nd |
| Intestinal IgG | | | | | | | |
| Vit A | <4 | <4 | 4.6 | 17.2 | 16.1 | nd | 16.0 |
| Vit C | <4 | <4 | 16.0 | 6.0 | 5.2 | nd | 16.0 |
| Vit D | <4 | <4 | <4 | 12.2 | 14.6 | nd | 14.0 |
| Miliboise | 5.0 | 27 | 75 | 76 | 38.3 | 4.3 | nd |
| Sorbitol | 50 | 74 | 64 | 93 | 294 | 257 | nd |
| Intestinal IgA | | | | | | | |
| Vit A | <4 | <4 | 4.0 | 26.9 | 32.1 | nd | 16.0 |
| Vit C | <4 | 4.6 | 55 | 337 | 1024 | nd | 776 |
| Vit D | <4 | <4 | 16.0 | 147 | 25.2 | nd | 36.7 |
| Miliboise | 7.6 | 39 | 65 | 159 | 58.0 | 16.0 | nd |
| Sorbitol | 52 | 51 | 67 | 111 | 178 | 180 | nd |

~, dose in $\mu$g, vitamins: +, dose in mM, sugars
*see Table 2.1

TABLE 2.6

Effect of orally administered dietary molecules on the immune response to oral antigen (LTB)*

| Dietary molecule | Day 21 Immune response per dose ($\mu$g~,mM+) | | | | | | |
|---|---|---|---|---|---|---|---|
| | 0.1 | 1.0 | 10 | 50 | 100 | 500 | 1000 |
| Serum IgG | | | | | | | |
| Vit B6 | 2352 | 5048 | 55.7 | 10.5 | 4.6 | nd | 4.0 |
| Lactose | 1782 | 1782 | 73.5 | 6.9 | 4.0 | 4.0 | nd |
| Sorbitol | 1024 | 256 | 18.3 | 13.9 | 4.0 | 4.0 | nd |
| Serum IgA | | | | | | | |
| Vit B6 | <4 | <4 | <4 | <4 | <4 | nd | <4 |
| Lactose | <4 | <4 | <4 | <4 | <4 | <4 | nd |
| Sorbitol | <4 | 1.4 | <4 | <4 | <4 | <4 | nd |
| Intestinal IgG | | | | | | | |
| Vit B6 | <4 | <4 | <4 | <4 | <4 | nd | <4 |
| Lactose | <4 | <4 | <4 | <4 | <4 | <4 | nd |
| Sorbitol | <4 | <4 | <4 | <4 | <4 | <4 | nd |
| Intestinal IgA | | | | | | | |
| Vit B6 | 5.6 | <4 | <4 | <4 | <4 | nd | <4 |
| Lactose | 4.0 | 4.0 | <4 | <4 | <4 | <4 | nd |
| Sorbitol | 4.0 | <4 | <4 | <4 | <4 | <4 | nd |

~, dose in $\mu$g, vitamins: +, dose in mM, sugars
*see Table 2.1

TABLE 2.7

Effect of varying the dose of co-administered dietary molecules on the immune response to intramuscularly presented antigen K99, 987P*

| Antigen given | Dietary molecule | Day 21 Immune response | | | | | |
|---|---|---|---|---|---|---|---|
| (s) IgG | (ug) | 0.1 | 1.0 | 10 | 50 | 100 | 1000 |
| K99 | Vit B12 | 1121 | 1468 | 1572 | 2328 | 4766 | 2109 |
| K99 | Vit D | 1024 | 1272 | 1168 | 1372 | 1489 | 1315 |
| 987P | Vit C | 1687 | 1529 | 1707 | 1700 | 1662 | 1891 |
| (s) IgG | (mM) | 0.1 | 1.0 | 10 | 50 | 100 | 500 |
| K99 | Melibiose | 1024 | 1176 | 1057 | 1392 | 1262 | 989 |
| 987P | Melibiose | 1538 | 1622 | 1701 | 1519 | 1666 | 1621 |
| 987P | Sorbitol | 1670 | 1577 | 1548 | 1632 | 1711 | 1651 |

+. no serum IgA, intestinal IgG or intestinal IgA was detected
*See Table 2.1

EXAMPLE 3

The two previous examples demonstrated that small doses of orally administered mucosal immunogens have the capacity to induce significant serum IgG titers with or without a parallel rise in secretory IgA antibody levels. Furthermore, it was shown that the immune response can be tailored by the co-administration of dietary molecules. The finding that the lectins used in the first study were capable of acting as carriers to prime for an anti-DNP response suggested that the potential exists for at least some of these mucosal immunogens to act as "carriers" for other antigens, therefore improving the relatively poor uptake of most antigens across the intestinal epithelium.

The following study was designed to investigate whether this carrier potential exists and to establish some of the various parameters for its successful use as a means of formulating new and more effective oral vaccines and/or orally administered drugs.

Materials and Methods

Conjugation of antigens to the mucosal immunogens

Dinitrophenylation of carriers

DNFB was reacted with Lectins and carrier as described above (see general methods)

Lipopolysaccharide (LPS) and polysaccharide (PS conjugation

*S. typhimurium* LPS and PS were purified as described previously (accompanying examples). LPS and PS were coupled to the MI using the periodate method (Avrameus and Ternynck, 1971).

Glutaraldehyde coupling

Leutinizing hormone releasing hormone (LHRH), bovine serum albumin (BSA) (from Sigma Chemical co. St. Louis, Mi.) and *S. typhimurium* flagella were individually coupled to MI using the two step glutaraldehyde procedure of Ayrameus et al (1978). Briefly, the required protein was reacted with 0.2% glutaraldehyde for 2 hrs at R.T. proteins were dialysed overnight against carb/bicarb buffer pH 9.5 followed by the addition of MI at molar ratio's of 5, 10, 20 and 40:1, Antigen:MI, as required and reacted for 24 hrs at RT. Finally ethanclamine (Sigma) was added to a final concentration of 0.1M, (1 hr, RT) followed by overnight dialysis at 4C against 0.1 M carb/bicarb buffer pH 9.5.

Peroxidase conjugated lectins

Commercial preparations of peroxidase conjugated to the lectins from *Glycine max, Arachis hypogea, Tetragonolobus purpureas* and conconavalin A were purchased from Sigma.

Chemical synthese of LHRH conjugates

LHRH was conjugated to LTB using the glutaraldehyde procedure outlined above. Glutaraldehyde activated LHRH was added to LTB at a ratio of 20:1 LHRH:LTB and allowed to couple O/N at R.temp. The resultant conjugate was dialysed extensively against 0.1 M Carb/bicarb buffer pH 9.5 before feeding. Controls consisted of LHRH or LTB which had been treated with glutaraldehyde alone.

TABLE 3.1

Antibody response to DNP-modified mucosal Immunogens.

| | | Immune response* | | | |
|---|---|---|---|---|---|
| | Dose | Anti-DNP | | Anti-Carrier | |
| Immunogen | (μg) | serum IgG | Int IgA | serum IgG | Int IgA |
| K99 | 20 | <4 | <4 | 875 ± 62 | 3.9 ± 5.1 |
| K99 | 100 | <4 | <4 | 1351 ± 128 | 16.7 ± 2.3 |
| DNP6.K99 | 20 | 21 ± 10.5 | <4 | 64 ± 7.2 | <4 |
| DNP18.K99 | 500 | 1024 ± 77 | 42 ± 9.6 | 128 ± 27.4 | 76 ± 12.9 |
| DNP1.8.K99 | 500 | 1176 ± 164 | 28 ± 14.4 | 3565 ± 192 | 88 ± 21.0 |
| 987P | 20 | <4 | <4 | 891 ± 76 | 27.8 ± 13.6 |
| 987P | 100 | <4 | <4 | 1024 ± 89 | 84 ± 22.4 |
| DNP6.987P | 20 | 24 ± 3.1 | <4 | 147 ± 12.2 | <4 |
| DNP25.987P | 500 | 1024 ± 244 | 14 ± 3.1 | 111 ± 34.1 | 68 ± 19.2 |
| DNP2.5.987P | 500 | 1351 ± 196 | 7 ± 1.4 | 2048 ± 166 | 128 ± 38.4 |
| LTB | 20 | <4 | <4 | 1351 ± 211 | 12.2 ± 4.4 |
| DNP2.3.LTB | 20 | 24.3 ± 5.6 | <4 | 445 ± 35 | <4 |
| LTB | 100 | <4 | <4 | 891 ± 56 | 4.0 |
| DNP6BSA | 20 | <4 | <4 | <4 | <4 |
| DNP6BSA | 100 | <4 | <4 | <4 | <4 |
| Con A** | 20 | 666 ± 84 | <4 | nd | nd |
| PW-mitogen** | 20 | 641 ± 119 | <4 | nd | nd |
| L. culinaris** | 20 | 954 ± 48 | <4 | nd | nd |
| H. pomatia** | 20 | 591 ± 127 | <4 | nd | nd |
| P. vulgaris** | 20 | 1378 ± 110 | 4.8 ± 2.3 | nd | nd |
| G. max** | 20 | 1529 ± 65 | 3.1 ± 6.9 | nd | nd |
| A. hypogea** | 20 | 1276 ± 242 | <4 | nd | nd |
| U. europeus** | 20 | 1583 ± 94 | <4 | nd | nd |

*The reciprocal of the antiserum dilution that gave on ELISA reading of 0.5 after 45 min at 37 C. Each value represents the mean of 5 mice ± 1 standard deviation.
**Each lectin was substituted with 4 DNP groups

TABLE 3.2

Carrier potential of K99 for various antigens

| | | | Immune Response* | | | |
|---|---|---|---|---|---|---|
| | | | Antigen | | Carrier | |
| Immunogen | Molar Ratio | Dose ($\mu$g) | Serum IgG | Int IgA | Serum IgG | Int IgA |
| K99 | — | 20 | <4 | <4 | 875 ± 62 | 3.9 ± 5.1 |
| K99 | — | 100 | <4 | <4 | 1351 ± 94 | 16.7 ± 2.8 |
| BSA-K99 | 1:4 | 20 | <4 | <4 | <4 | <4 |
| BSA-K99 | 1:5 | 500 | <4 | <4 | 73.5 ± 11.2 | <4 |
| BSA-K99 | 1:10 | 500 | <4 | <4 | 147 ± 48.2 | <4 |
| BSA-K99 | 1:20 | 500 | 222 ± 47 | 126 ± 29.2 | 3809 ± 226 | 84 ± 16.6 |
| BSA-K99 | 1:40 | 500 | 73 ± 19.6 | 44 ± 7.5 | 3176 ± 391 | 64 ± 11.9 |
| Flag-K99 | 1:5 | 20 | <4 | <4 | <4 | <4 |
| LPS-K99 | 1:1** | 20 | <4 | <4 | <4 | <4 |
| PS-K99 | 1:1** | 20 | <4 | <4 | 229 ± 101 | 5.2 ± 2.6 |
| BSA | — | 20 | <4 | <4 | — | — |
| Flagellae | — | 20 | <4 | <4 | — | — |
| LPS | — | 20 | 12.1 ± 2.7 | <4 | — | — |
| PS | — | 20 | <4 | 4.2 ± 0.4 | — | — |

*See Table 3.1
**Ratio based on weight.

TABLE 3.3

Carrier potential of 987P for various antigens

| | | | Immune Response* | | | |
|---|---|---|---|---|---|---|
| | | | Antigen | | Carrier | |
| Immunogen | Molar Ratio | Dose ($\mu$g) | Serum IgG | Int IgA | Serum IgG | Int IgA |
| 987P | — | 20 | <4 | <4 | 891 ± 76 | 27.8 ± 13.6 |
| 987P | — | 100 | <4 | <4 | 1024 ± 83 | 84 ± 26.7 |
| BSA-987P | 1:4 | 20 | <4 | <4 | 84 ± 2.6 | <4 |
| BSA-987P | 1:5 | 500 | <4 | <4 | 256 ± 49 | <4 |
| BSA-987P | 1:10 | 500 | 29.8 ± 7.4 | 4.6 ± 2.2 | 675 ± 110 | <4 |
| BSA-987P | 1:20 | 500 | 306 ± 88 | 122 ± 47.6 | 4263 ± 408 | 194 ± 38.6 |
| BSA-987P | 1:40 | 500 | 124 ± 47 | 110 ± 38.4 | 4705 ± 521 | 156 ± 55 |
| Flag-987P | 1:5 | 20 | 1552 ± 361 | <4 | — | — |
| LPS-987P | 1:1** | 20 | <4 | <4 | 194 ± 28.6 | <4 |
| PS-987P | 1:1** | 20 | <4 | <4 | 337 ± 96 | 5.2 ± 6.8 |
| BSA | — | 20 | <4 | <4 | — | — |
| Flagellae | — | 20 | <4 | <4 | — | — |
| LPS | — | 20 | 12.1 ± 2.7 | <4 | — | — |
| PS | — | 20 | <4 | 4.2 ± 0.4 | — | — |

*See Table 3.1
**Ratio based on weight.

TABLE 3.4

Effects of altering dosage of substituted carrier on the immune response

| | Dose | Immune Response (Serum IgG)* | |
|---|---|---|---|
| Antigen | ($\mu$g) | Anti-BSA | Anti-Carrier |
| BSAO.03.K99 | 70 | 13.9 ± 4.4 | 776 ± 148 |
| BSAO.03.K99 | 140 | 36.7 ± 14.6 | 1782 ± 174 |
| BSAO.03.K99 | 280 | 73.5 ± 22.1 | 1989 ± 215 |
| BSAO.05.987P | 70 | 36 ± 2.6 | 891 ± 109 |
| BSAO.05.987P | 140 | 168 ± 23.7 | 1552 ± 176 |
| BSAO.05.987P | 280 | 337 ± 43.7 | 2042 ± 180 |

*See Table 2.1

TABLE 3.5

Effect of chemically conjugated LHRH-LTB on reproductive organs of the female mouse*

| Conjugate + uterus | Coupling | Route procedure | Dose | No | Body ($\mu$g) | Ovaries Mice weight | % Body wt |
|---|---|---|---|---|---|---|---|
| LHRH-LTB | glut | os/os | 20 | 5 | 21.19 | 0.03 | 0.17% |
| LHRH-LTB | glut | os/os | 50 | 5 | 21.16 | 0.04 | 0.23% |
| LHRH | glut | os/os | 50 | 6 | 20.13 | 0.11 | 0.62% |
| LTB | glut | os/os | 50 | 3 | 18.18 | 0.14 | 0.76% |
| LHRH-LTB | glut | im/im | 50 | 6 | 20.16 | 0.16 | 0.97% |
| LHRH, LTB | mix | os/os | 50 | 7 | 27.32 | 0.15 | 0.55% |
| LHRH, LTB | mix | im/im | 50 | 7 | 30.07 | 0.26 | 0.73% |

TABLE 3.5-continued

Effect of chemically conjugated LHRH-LTB on reproductive organs of the female mouse*

| Conjugate + uterus | Coupling O + U/ | Route procedure | Dose | No | Body (μg) | Ovaries Mice weight | % Body wt |
|---|---|---|---|---|---|---|---|
| LTB | — | os/os | 50 | 7 | 28.26 | 0.24 | 0.87% |
| — | — | os/os | — | 5 | 19.19 | 0.16 | 0.82% |

*Animals received antigen on days 0 and 14. On day 28 mice were euthanased and their reproductive tracts weighed.

TABLE 3.6

Effect of genetically constructed LHRH conjugates on the reproductive organs of the female mouse

| Conjugate | Route | Dose (μg) | Body weight | Ovaries + uterus | % Body wt O + U/tot* |
|---|---|---|---|---|---|
| B-gal-(LHRH)3.5 | im/im | 20 | 19.47 | 0.10 | 0.49 |
| B-gal-(LHRH)3.5 | im/im | 20 | 13.44 | 0.10 | 0.56 |
| B-gal-(LHRH)3.5 | im/im | 50 | 19.39 | 0.10 | 0.54 |
| LTB-(LHRH)3.5 | os/os | 20 | 19.35 | 0.08 | 0.39 |
| LHRH | os/os | 20 | 19.34 | 0.10 | 0.44 |
| LHRH | im/im | 20 | 19.39 | 0.15 | 0.76 |
| — | im/im | — | 17.74 | 0.03 | 0.46 |
| — | os/os | — | 18.63 | 0.11 | 0.60 |

For all intramuscular injections antigens were administered in montanide. Im/im controls received montanide/saline mixtures.
*Animals received antigen on days 0 and 14. On day 28 mice were euthanased and their reproductive tracts weighed.

Genetic fusion of LHRH to B-galactosidase and LTB

CONSTRUCTION OF A PLASMID VECTOR EXPRESSING A FUSED LTB/LHRH HYBRID POLYPEPTIDE

1. DNA Fragment Containing LTB Coding Sequences

A Hind III fragment was obtained from a pBR322 based plasmid containing the cloned LTB gene (Leong et al, 1985), from the plasmid NP307 in *E. coli* strain RC411 (Dallus et al, 1979) which had been modified, using a Spe I site near the stop codon for LTB, and then mung bean nuclease digestion, using standard conditions. (Unless specified otherwise, the conditions used for standard recombinant DNA techniques and nucleic acid modifying enzymes are as described in Molecular Cloning, A Laboratory Manual, Maniatis, Fritsch and Sambrook. Cold Spring Harbor Laboratory, 1982). This eliminated the stop codon normally found after amino acid 123 in LTB, removing 9 base pairs of DNA and fortuitously generating a Hind III site as shown below (SEQ ID NOS:1&2)

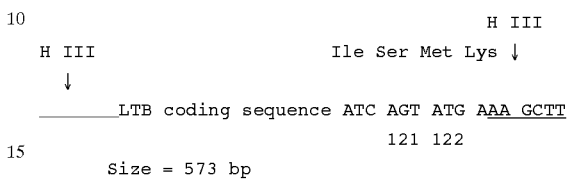

```
                                        H III
H III                        Ile Ser Met Lys ↓
 ↓
_____LTB coding sequence ATC AGT ATG AAA GCTT
                                       121 122
     Size = 573 bp
```

This fragment was ligated into the vector pUC13 (Messing, 1983) after Hind III digestion and phosphatase treatment of the plasmid using standard conditions. This served to place the remaining polylinker region of pUC13, including a PstI, SalI, XbaI, BamHI, SmaI, SstI and EcoRI sites downstream of the LTB sequence containing DNA insert.

2. Creation of Synthetic LHRH Coding Oligonucleotides

Two oligonucleotides, of 30 bases in length, with sequences described in A and B below, were designed to form overlapping hybrid duplexes, as shown in C, which result in a duplex which will encode linear end to end repeats of the 10 amino acids encoding the peptide hormone LHRH (Schally and Coy, 1983). Role of Peptides and Proteins in Control of Reproduction, McCann and Dhindsa eds, Elsevier Science Publishing Co, Inc. pp 89–110). In this sequence, glutamic acid replaces the normal N-terminal pyroglutamic acid.

```
A.  5'  GAG CAC TGG TCC TAC GGC CTT CGA CCC GGG    3' (SEQ ID NO:3)
B.  5'  GTA GGA CCA GTG CTC CCC GGG TCG AAG GCC    3' (SEQ ID NO:3)
C.         ⌊  A  ⌋   ⌊  A  ⌋   ⌊  A  ⌋
              ⌈ B ⌉    ⌈ B ⌉           etc.
```

The oligonucleotides were annealed together for 1 hr at 40° C. in 50 mM NaCl, 10 mM Tris pH 7.5, end filled with Klenow, and then the mixture was ligated into SmaI cut M13 mp18, using standard procedures. M13 phage containing inserts were isolated, and the DNA sequences of the inserts were determined by the dideoxy technique. One recombinant, designated as P29, was chosen for the fused construct. Its DNA sequence, together with the amino acids it encodes, in the region of the insert at the SmaI site is given below (SEQ ID NOS:5&6).

N terminus of β-galactosidase, α fragment

```
Met Thr Met Ile Thr Asn Ser Ser Ser Val Pro Leu Arg
ATG ACC ATG ATT ACG AAT TCG AGC TCG GTA CCC CTT CGA
```

```
                             -continued
                         EcorI
Pro Gly Glu His Trp Ser Tyr Gly Leu Arg Pro Gly
CCC GGG GAG CAC TGG TCC TAC GGC CTT CGA CCC GGG
    <--------------------1------------------>
Clu His Trp Ser Tyr Gly Leu Arg Pro Gly Glu His Trp
GAG CAC TGG TCC TAC GGC CTT CGA CCC GGG GAG CAC TGG
    <----------------------2------------------>  <-------------
Ser Tyr Gly Leu Arg Pro Gly Gly Asp Pro Leu Glu Ser Thr
TCC TAC GGC CTT CGA CCC GGG GGG GAT CCT CTA GAG TCG ACC
---3 ---------------------->                        HindII
```

The DNA sequence confirmed the insertion of DNA from the synthetic oligonucleotides to place an in-frame fusion of approximately 3 and a half repeats of the LHRH encoding sequence (34 amino acids). The complete LHRH coding blocks are indicated by the arrows.

The replicative from DNA of P29 was digested with EcoRI and HincII (sites indicated in DNA sequence above), and end filled using standard conditions. The small 140 base pair fragment was isolated from a polyacrylamide gel.

3. Construction of the LTB/LHRH Fusion Vector

The pUC13 plasmid containing the LTB coding sequence inserted in the HindIII site (section 1 above) was digested with SalI, end filled and phosphatased using standard conditions. The vector DNA was then ligated to the end filled EcoRI/HincII fragment from P29 (Section 2 above). The fusion should have the amino acid sequence below (SEQ ID NO:7).

aa1—122 (lys)-ala-trp-ala—ala-gly-arg-asn-ser—ser—ser-val-pro-LTB coding sequence.

leu-arg-pro-gly-[glu-his-trp-ser-tyr-gly-leu-arg-pro-gly]$_3$-LHRH gly-asp-pro-leu-glu-ser-arg-leu There is a stop codon 24 bases beyond the LHRH sequence which defines the production of a 176 amino acid polypeptide, with 122 amino acids from LTB, 34 amino acids encoding the LHRH repeat, and an additional 20 amino acids derived from the adjoining regions.

The correct construct was screened by digesting DNA from minipreps with Eco RI and looking for plasmids with the appropriately larger Eco RI fragment. The putative positives were further screened for the expression of this polypeptide, driven from the lac promoter of pUC13. Bacterial extracts were analysed on polyacrylamide gels followed by transfer to nitrocellulose paper and Western blotting with rabbit antisera directed against an LTB and LHRH conjugate. A peptide of the expected size was detected by both antisera.

4. Construction of expression plasmid K66 and expression strain BTA1185

A 573 bp Eco RI fragment of the pUC13 LTB-LHRH fusion plasmid described in 3, which contains the LTB-LHRH fusion coding region in its entirity, was isolated from an agarose gel and ligated into Eco RI cut, phosphatased expression vector pKK223-3 (from Pharmacia). The resultant expression plasmid PBTA K66, placed the expression of the fusion protein under the control of the tac promoter, where expression is induced with IPIG. The plasmid was transformed into $E.$ $coli$ host strain JM101 (SupE, thi, (lac-pro AB) [F' traD36, pro AB lacI$^q$ Z M 15) to give the host vector expression system BTA1185.

5. Production and Purification of LTB/LHRH Fusion Protein for Animal Trials

The LTB(LHRH)$_{3.5}$ producing strain was grown as described previously. After induction with IPTG for 2 h bacteria were pelleted by centrifugation (3,000×g, 10 min at 4° C.). Bacteria were then resuspended in dH$_2$O and lysed in a French Press. After removal of the bacterial debris by centrifugation (18,000×g, 10 min, at 4° C.) the supernatant was loaded onto an agthio-galactose column (Sigma). The fusion protein was then eluted with 0.5M galactose and dialysed against 0.1M carb/bicarb buffer pH 9.5.

Antigen administration and measurement of the immune response

All oral presentation procedures, antibody collections and ELISA determinations were as described previously.

RESULTS

Demonstration of the carrier potential of the mucosal immunogens

All of the mucosal immunogens tested showed the capacity to effectively transport the covalently attached hapten DNP across the intestinal mucosa and to elicit a serum anti-DNP Ab response after feeding of the dinitrophenylated-MI. DNP-modified BSA, however was completely ineffective in eliciting an anti-DNP or anti-BSA response when fed at the concentrations tested (Table 3.1). Initial experiments in which K99 and 987P were complexed to much larger molecules than DNP were unsuccessful in generating immune responses to either the mucosal immunogen or to the molecule coupled to it (Tables 3.2 & 3.2), possibly due to steric interference in the binding of the pili to the mucosal epithelium. It was therefore decided to vary the ratio of antigen to MI. When various ratios of BSA:pili were tested, it was found that when ratios of greater than 1:20 BSA:pili were fed it was not possible to generate either anti-BSA or anti-pili responses even with a dose of 500 ug, demonstrating that it was not possible for the complexes to effectively associate with the mucosal epithelium and to therefore generate an immune response. However when ratios of 1:20 or 1:40 were employed good responses to both BSA and to pili were observed (Tables 3.2 & 3.3). The magnitude of the immune response was readily varied by altering the doses of complex fed (Table 3.4).

Oral administration of LHRH coupled to LTB lead to a significant reduction in the combined uterine and ovarian weights of female mice receiving either 20 or 50 ug LHRH-LTB (P 0.05) (Table 3.5,3.6). No such weight loss was seen with either LHRH or LTB fed alone or together or to intramuscular injection of LHRH-B-galactosidase, LHRH-LTB, or free LHRH. The effect of the weight loss was also seen developmentally as there was a complete absence of mature follicules in the ovaries, thus, the animals were effectively "castrated". There was a slight reduction in reproductive tract weights when mice were fed the genetically constructed LTB-(LHRH)$_{3.5}$ fusion protein (Table 3.6) but in this experiment, the reduction was not significant at the doses tried.

EXAMPLE 4

Induction of cell-mediated immunity after oral administration of antigen

Feeding of mucosal immunogens was shown to be effective in eliciting humoral responses as measured by the production of serum and intestinal antibodies. It was not known, however whether there was a concomitant stimulation of a cell mediated immune (CMI) response to the mucosal immunogens.

The following study was designed to compare the CMI generated by oral presentation of a mucosal immunogen with that generated by classic subcutaneous (s.c.) injection of antigen in Complete Freund's Adjuvant (CFA).

Methods

Male C5781/6J mice were immunized by feeding 20 $\mu$g antigen in 0.1 M carb/bicarb buffer pH 9.65 or by injecting 20 $\mu$g antigen in CFA s.c. Controls received only buffer or adjuvant. Seven days after immunization mice were injected in the left back footpad with 10 $\mu$g of antigen in 20 $\mu$l saline, and injected with 20 $\mu$l saline alone in the right rear footpad. After a further 24 hours, the difference in thickness between the left and right rear footpads was measured using a micrometer.

Results

The results shown in table 4.1 demonstrates that a good cellular immune response is generated upon oral feeding of either 987P or LTB mucosal immunogens. In fact the response was suprisingly high as it was only slightly smaller than that generated by the s.c. injection of these antigens in CFA.

TABLE 4.1

Generation of a cell mediated immune resonse upon oral presentation of mucosal immunogens.

| Antigen | Control | Immunisation route | |
|---|---|---|---|
| | | Oral | Subcutaneous |
| 987P | 11 ± 2 | 31 ± 6.6 | 38 ± 5 |
| LTB | 5 ± 4.5 | 14 ± 3.7 | 26 ± 5.8 |

*Results represent the increase in footpad size after immunization with antigen. Results are the mean of 5 mice ± standard deviation.

INDUSTRIAL APPLICABILITY

Industrial applications of the invention include the preparation of oral medicaments for administration to vertebrate hosts.
Potential Vaccine Candidates for Oral Vaccine

| | |
|---|---|
| Allergens: | Various Grass Pollens: barley, couch |
| | Weed Pollens: clover, dock |
| | Tree Pollens: ash, cyprus |
| | Plant Pollens: broom |
| | Epithelia: car hair, dog hair, pig hair |
| | Miscellaneous: house dust, wheat chaff, Kapok. |
| Hormones: | LHRH, FSH, HGH, Inhibin |
| Vaccines: | Haemagglutunins from |
| | Influenza, Measles, Rubella, Smallpox, Yellow Fever, Diphtheria, Tetanus, Cholera, Plague, Typhus, BCG, *Haemophilus influenzae*, *Neisseria catarrhalis*, *Klebsiella pneumoniae*, Pneumococci, streptococci esp. *S. mutans*. |
| Pili from: | *E. Coli*, *N. gonorrhoeae*, *N. meningitis*, *N. catarrhalis*, Yersinia spp., *Pseudomonas aeruginosa*, Pseudomonas spp., *Moraxella bovis*, *Bacteroides nodosus*, Staph spp., Strep spp. Bordetella spp.? |

REFERENCES

AVREMEAS, S., Ternynck, T. & Geudson, J.-L. 1978 Coupling of enzymes to antibodies and antigens. Scand. J. Immunol., 8. supl. 7, 7–23.

AVRAMEAS, S. & Ternynck, T. 1971 Peroxidase labelled antibody and Fab conjugate with enhanced intracellular penetration. Immunochem., 8, 1175–1179.

BEFUS, A. D., and J. Bienenstock. 1982. Factors involved in symbiosis and host resistance at the mucosa-parasite interface. Prog. Allergy. 31:76.

BIENENSTOCK, J., and A. D. Befus. 1980. Mucosal Immunology. Immunology. 41:249.

BLAKE, J. S., and E. C. Gotschlich. 1984. Purification and partial characterization of the opacity-associated proteins of *Neisseria gonorrhoeae*. 159:452.

BLAND, P. W. & Britton, D. C. (1984) Morphological study of antigen-sampling structures in the rat large intestine. Infect. Immun., 43, 693–699.

CLARK, S., A. Cahill, C. Stirzaker, P. Greenwood and R. Gregson. 1985. Prevention by vaccination-animal bacteria, p. 481–487. In S. Tzipori (ed.) Infectious diarrhoea in the young. Elsevier Science Publishers B.V.

CONTEY, J. R., and L. R. Inman. 1981. Diarrhea due to *Escherichia coli* strain RDEC-1 in the rabbit. The Peyer's patch as the initial site of attachment and colonization. J. Infect. Dis. 43:440.

DALLAS et. al. (1979) Cistrons encoding *Escherichia coli* heat labile toxin J. Bact. 139 850–858.

ELSON, C. O. & EALDING, W. (1984a) Generalized systemic and mucosal immunity in mice after mucosal stimulation with cholera toxin. J. Immunol., 132, 2736–2741.

ELSON, C. O. & EALDING, W. (1984b) Cholera toxin did not induce oral tolerance in mice and abrogated oral tolerance to an unrelated antigen. J. Immunol. 133, 2892–2897.

EVANS, D. G. & Evans, D. J. (1978) New surface-associated heat-labile colonization factor antigen (CFA/II) produced by enterotoxigenic *Escherischia coli* of serogroups O6 and O8. Inf. Immun., 21, 538–647.

De GRAAF, F. K., P. Klemm, and W. Gaastra. 1981. Purification, characterization and partial covalent structure of the adhesive antigen K99 of *Escherichia coli*. Infect. Immun. 33:377.

De GRAAF, F. K. & Roorda, I. (1882) Production, purification, and characterization of the fimbrial adhesive antigen F41 isolated from calf enterooathogenic *Escherichia coli* strain B41M. Infect. Immun., 36, 751–758.

FUJITA, K. & Finkelstein, R. A. 1972 Antitoxic immunity in experimental Cholera. J. Infect. Dis., 125, 647–655.

FUSCO, P., A. To, S. To, and C. Brinton, Jr. 1978. The purification and characterisation of four types of *E. Coli* pili and the specificity of *E. coli* pili for immunity colonization and adhesion, p. 60–70. In C. Miller (ed.), XIIIth U.S. Japan Conference on Cholera, Atlanta, Ga., 1977. National institution of Health, Bethesda, Md.

GAASTRA, W., and F. K. de Graaf. 1982. Host specific fimbrial adhesion of noninvasive enterotoxigenic *Escherichia Coli* strains. Microbiol. Rev. 46:129.

GAASTRA, R. A. (1975) Anattempt to identify the intestinal receptor for the K88 ashesin by means of a haemagglutination inhibition test using glycoproteins and fractions and sow colostrum. J. Gen. Microbiol., 86, 228–240.

GIBBONS, R. A. (1975) Anattempt to identify the intestinal receptor for the K88 ashesin by means of a haemagglutination inhibition test using glycoproteins and fractions from sow colostrum. J. Gen. Microbiol., 86, 228–240.

HANSON, D. G., VAZ, N. M., MAIA, L. C. S. & LYNCH, J. M., (1979) Inhibition of specific immune responses by feeding protein antigens. J. Immunol., 123, 2337–2343.

HERBERT, D., P. J. Phipps, and R. E. Strange. 1985. Carbohydrate analyses, determination of total carbohydrate, p. 265–279. In J. R. Norris, and D. W. Ribben (ed.), Methods in Microbiology. v. 58.

ISAACSON, R. E., J. Colmenero, and P. Richter. 1981. *Escherichia coli* K99 pili are composed of one subunit species. FEMS Microbiol. Lett. 12:229.

ISAACSON, R. E., and P. Richter. 1981. *Escherichia Coli* 987P Pilus. Purification and partial characterization. J. bacteriol. 146:784.

KLIPSTEIN, F. A., ENGERT, R. F., & SHORT, H. B. (1980) Protective effect of immunization with heat-labile entertoxin in gnotobiotic rats monocontaminated with enterotoxigenic *Escherichia coli*. Inf. Immunol., 28, 163–170.

LAEMMLI, U. K. 1970. Cleavage of structural proteins during the assembly of the head of bacteriophage T4. Nature (Lond.) 227:680.

LEONG et. al. (1985) Nucleotide sequence comparison between heat labile toxin B-subunit cistrons from *Escherichia coli* of human and porcine origin Infection and Immunity 48 73–77.

LEVINE, M. M., Rennels, M. B., Daya, V. & Hughes, T. P. (1980) Haemagglutination and colonization factora in enterotoxigenic and enteropathogenic *Escherichia coli* that cause diarrhea. J. Inf. Dis., 141, 733–737.

LITTLE, J. R. & Eisen, H. N. (1967) Preparation of immunogenic 2,4-dinitrophenyl and 2,4,6-tritrophenyl proteins. In "Methods in Immunology and Immunochemistry" (Ed. Williams, C. A. & Chase, M. W.). I, p. 128. Academic Press, New York.

MESSIER, B., and C. P. Le Blond (1960). Cell proliferation and migration as revealed by radioautography after injection of thymidine —H3 into male rats and mice. An. J. Anat. 106:247.

MESSING (1983) New M13 Vectors for cloning Methods in Enzymology 101 20–78.

MORGAN, R. L., Isaacson, R. E., Moon, H. W., Brinton, C. C. & To, C.-C. (1978) Immunization of suckling pigs against enterotoxigenic *Escherichia coli*-induced diarrheal disease by vaccinating dams with purified 987 or K99 pili. Inf. Immun., 22, 771–777.

MORRIS, J. A., C. J. Thorns, and W. J. Sojka. 1980. Evidence for two adhesive antigens on the K99 reference strain *Escherichia coli* 341. J. Gen. Microbiol. 118:107.

MOWAT, A. McI., (1985) The role of antigen recognition and supressor cells in mice with oral tolerance to ovalbumin. Immun., 56, 253–260.

MOWAT, A. McI. & PARROT, D. M. V. (1983) Immunological responses to fed protein antigens in mice. Immun., 50, 547–554.

NGAN, J. & KIND, L. S., (1978) Suppressor T cells for IgE and IgG in peyer's patches of mice tolerant by the oral administration of ovalbumin. J. Immunol., 120, 861–865.

PIERCE, N. F. & KOSTER, F. T. (1980) Priming and suppression of the intestinal immune response to cholera toxoid/toxin by parenteral toxoid in rats. J. Immunol., 124, 307–311.

PIERCE, N. F., SACK, R. B., & SIRCAR, B. K., (1977) Immunity to experimental cholera. J. Inf. Dis., 135, 888–896.

RICHMAN, L. K., CHILLER, J. M., BROWN, W. R., HANSON, D. G. & NELSON, N. M. (1978) Enterically induced immunological tolerance. J. Immunol., 121, 2429–2434.

RICHMAN, L. K., A. S. Graeff, and W. Strober. 1981 Antigen presentation by macrophage enriched cells from the mouse Peyer's patch. Cell Immunol. 62:1100.

ROTHBREG R. M., KRAFT, S. C., & MICHALEK, S. J., (1973) Systemic immunity after local antigenic stimulation of the lymphoid tissue of the gastrointestinal tract. J. Immunol., Ill, 1906–1913.

RUSSELL-JONES, G. J., E. C. Gotschlich, and M. S. Blake. 1984. A surface receptor specific for human IgA on group B streptococci possessing the Ibc protein antigen. J. Exp. Med. 160:1467.

RUSSELL-JONES, G. J., and E. C. Gotschlich. 1984. Identification of protein antigens of group B streptococci, with special reference to the Ibc antigen. J. Exp. Med. 160 1476.

SALIT, I. E., M. Blake, and E. C. Gotschlich. 1980. Intrastrain heterogeneity of gonococcal pili is related to capacity colony variance. J. Exp. Med. 151:716.

SCHALLY AND COY (1983). Stimulatory and inhibitory analogues of LH-releasing hormone: Basic and clinical studies in Role of Peptides and Proteins in Control of Reproduction McCann and Dhindsa eds. Elsevie Science Publishing Co. Inc. pp89–110. Maniatis, Fritsch and Sambrook (1982) Molecular Cloning, Laboratory Manual. Cold Spring Harbour Laboratory.

SEVENNERHOLM, A. M. & Holmgren, J. 1978 Identification of *E. coli* heat-labile enterotoxin by means of a ganglioside immunosorbent assay (GM-1 ELISA) procedure. Curr. Microbiol. 1, 19–23.

TOMASI, T. B., (1980) Oral tolerance. Transplantation, 29, 353.

TONER, P. G., K. E. Carr, and G. M. Wyburn (1971). Intestine. In The Digestive System—An Ultrasonic Atlas and Review, Butterworths, London.

TSAI, C. M., and Frasch, C. E. 1982. A sensitive silver stain for detecting lipopolysaccharide in polyacrylamide gels. Anlal. Biochem., 119, 115–119. 175

---

What is claimed is:

1. A protein conjugate comprising an immunogen covalently linked to a carrier molecule,
   wherein said carrier molecule is capable of specifically interacting with the mucosal epithelium of a vertebrate host, and
   wherein said protein conjugate retains both the ability of the immunogen to elicit an immune response in said vertebrate host and the capacity of the carrier molecule to specifically interact with the mucosal epithelium of said host, and wherein said protein conjugate elicits a serum and secretory immune response in said host following oral administration, without non-oral administration in Freund's adjuvant.

2. A protein conjugate according to claim 1, wherein said carrier molecule is heat labile toxin of enterotoxigenic *E. coli*.

3. A protein conjugate according to claim 1, wherein said carrier molecule is the binding subunit of heat labile toxin of enterotoxigenic *E. coli*.

4. A protein conjugate according to claim 1, wherein said immunogen is LHRH.

5. A protein conjugate according to claim 1, wherein said immunogen is FSH, HGH, or inhibin.

6. A protein conjugate according to claim 1, wherein said carrier molecule and said immunogen are chemically cross-linked.

7. A vaccine comprising a protein conjugate according to claim 1 and a pharmaceutically or veterinarally acceptable adjuvant, diluent, or excipient.

8. A protein conjugate according to claim 1, wherein said immunogen is an allergen.

9. A protein conjugate according to claim 8, wherein said allergen is selected from the group consisting of pollen, animal hair, animal spithelium, house dust, wheat chaff and kapok.

10. A protein conjugate according to claim 1, wherein said immunogen is a surface protein from an disease-causing agent selected from the group consisting of influenza, measles, Rubella, smallpox, yellow fever, diphtheria, tetanus, cholera, plague, typhus, BCG, *Haemophilus influenzae, Neisseria catarrhalis, Klebsiella pneumoniae, pneumococci,* and *streptococci*.

11. A protein conjugate according to claim 1, wherein said immunogen is a pilus from an organism selected from the group consisting of *E. coli, N. gonorrheae, N, neningitidis, N. catarrhalis, yersinia, pseudomonas, moraxella bovis, bacteroides nodosus, staphylococcus, streptococcus,* and *bordetella*.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: other nucleic acid

```
        (iv) ANTI-SENSE: NO (ix) FEATURE:
              (A) NAME/KEY: CDS
              (B) LOCATION: 1..12

(xi) SEQUENCE DESCRIPTION: SEQ ID NO:1:

ATC AGT ATG AAA GCTT                                                    16
Ile Ser Met Lys
 1

(2) INFORMATION FOR SEQ ID NO:2:

(i) SEQUENCE CHARACTERISTICS:
              (A) LENGTH: 4 amino acids
              (B) TYPE: amino acid
              (D) TOPOLOGY: linear (ii) MOLECULE TYPE: protein (xi) SEQUENCE DESCRIPTION: SEQ ID NO:2:

Ile Ser Met Lys
 1

(2) INFORMATION FOR SEQ ID NO:3:

(i) SEQUENCE CHARACTERISTICS:
              (A) LENGTH: 30 base pairs
              (B) TYPE: nucleic acid
              (C) STRANDEDNESS: unknown
              (D) TOPOLOGY: unknown (ii) MOLECULE TYPE: other nucleic acid (xi) SEQUENCE DESCRIPTION: SEQ ID NO:3:

GAGCACTGGT CCTACGGCCT TCGACCCGGG                                         30

(2) INFORMATION FOR SEQ ID NO:4:

(i) SEQUENCE CHARACTERISTICS:
              (A) LENGTH: 30 base pairs
              (B) TYPE: nucleic acid
              (C) STRANDEDNESS: unknown
              (D) TOPOLOGY: unknown (ii) MOLECULE TYPE: other nucleic acid (xi) SEQUENCE DESCRIPTION: SEQ ID NO:4:

GTAGGACCAG TGCTCCCCGG GTCGAAGGCC                                         30

(2) INFORMATION FOR SEQ ID NO:5:

(i) SEQUENCE CHARACTERISTICS:
              (A) LENGTH: 156 base pairs
              (B) TYPE: nucleic acid
              (C) STRANDEDNESS: unknown
              (D) TOPOLOGY: unknown (ii) MOLECULE TYPE: other nucleic acid (ix) FEATURE:
              (A) NAME/KEY: CDS
              (B) LOCATION: 1..156

(xi) SEQUENCE DESCRIPTION: SEQ ID NO:5:

ATG ACC ATG ATT ACG AAT TCG AGC TCG GTA CCC CTT CGA CCC GGG GAG          48
Met Thr Met Ile Thr Asn Ser Ser Ser Val Pro Leu Arg Pro Gly Glu
 5               10                  15                  20
```

```
CAC TGG TCC TAC GGC CTT CGA CCC GGG GAG CAC TGG TCC TAC GGC CTT      96
His Trp Ser Tyr Gly Leu Arg Pro Gly Glu His Trp Ser Tyr Gly Leu
            25                  30                  35

CGA CCC GGG GAG CAC TGG TCC TAC GGC CTT CGA CCC GGG GGG GAT CCT     144
Arg Pro Gly Glu His Trp Ser Tyr Gly Leu Arg Pro Gly Gly Asp Pro
            40                  45                  50

CTA GAG TCG ACC                                                     156
Leu Glu Ser Thr
        55
```

(2) INFORMATION FOR SEQ ID NO:6:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:6:

```
Met Thr Met Ile Thr Asn Ser Ser Val Pro Leu Arg Pro Gly Glu
 1               5                  10                  15

His Trp Ser Tyr Gly Leu Arg Pro Gly Glu His Trp Ser Tyr Gly Leu
            20                  25                  30

Arg Pro Gly Glu His Trp Ser Tyr Gly Leu Arg Pro Gly Gly Asp Pro
            35                  40                  45

Leu Glu Ser Thr
        50
```

(2) INFORMATION FOR SEQ ID NO:7:

(i) SEQUENCE CHARACTERISTICS:
        (A) LENGTH: 55 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:7:

```
Lys Ala Trp Ala Ala Gly Arg Asn Ser Ser Val Pro Leu Arg Pro
 1               5                  10                  15

Gly Glu His Trp Ser Tyr Gly Leu Arg Pro Gly Glu His Trp Ser Tyr
            20                  25                  30

Gly Leu Arg Pro Gly Glu His Trp Ser Tyr Gly Leu Arg Pro Gly Gly
            35                  40                  45

Asp Pro Leu Glu Ser Arg Leu
        50              55
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:8:

```
Ala Ala Thr Thr Val Asn Gly Gly Thr Val His Phe Lys Gly Glu Val
 1               5                  10                  15

Val Asn Ala Ala
        20
```

(2) INFORMATION FOR SEQ ID NO:9:

(i) SEQUENCE CHARACTERISTICS:
        (A) LENGTH: 22 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:9:

```
Trp Met Thr Gly Asp Phe Asn Gly Ser Val Asp Ile Gly Gly Ser Ile
1               5                  10                  15
Thr Ala Asp Asp Tyr Arg
            20
```

(2) INFORMATION FOR SEQ ID NO:10:

(i) SEQUENCE CHARACTERISTICS:
        (A) LENGTH: 22 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:10:

```
Asn Thr Gly Thr Ile Asn Phe Asn Gly Lys Ile Thr Ser Ala Thr Cys
1               5                  10                  15
Thr Ile Glu Pro Glu Ala
            20
```

(2) INFORMATION FOR SEQ ID NO:11:

(i) SEQUENCE CHARACTERISTICS:
        (A) LENGTH: 22 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:11:

```
Ala Pro Val Glu Asn Asn Thr Cys Gln Ala Asn Leu Asp Phe Thr Gly
1               5                  10                  15
Lys Val Thr Ala Xaa Leu
            20
```

(2) INFORMATION FOR SEQ ID NO:12:

(i) SEQUENCE CHARACTERISTICS:
        (A) LENGTH: 22 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:12:

```
Phe Thr Leu Ile Glu Leu Met Ile Val Ile Ala Ile Val Gly Ile Leu
1               5                  10                  15
Ala Ala Val Ala Leu Pro
            20
```